United States Patent [19]

Yankee

[11] 4,096,342

[45] Jun. 20, 1978

[54] 8β,12α,15β-PGE$_2$ COMPOUNDS

[75] Inventor: Ernest W. Yankee, Portage, Mich.

[73] Assignee: The Upjohn Company, Kalamazoo, Mich.

[21] Appl. No.: 660,754

[22] Filed: Feb. 23, 1976

Related U.S. Application Data

[63] Continuation of Ser. No. 518,645, Oct. 29, 1974, abandoned, and a continuation-in-part of Ser. No. 289,317, Sep. 15, 1972, abandoned.

[51] Int. Cl.$^2$ .......................................... C07C 177/00
[52] U.S. Cl. ........................... 560/121; 260/514 D; 560/231
[58] Field of Search ................... 260/468 D, 514 D; 560/121, 231

[56] References Cited

U.S. PATENT DOCUMENTS 3,862,984  1/1975  Pike et al. ........................... 260/514

FOREIGN PATENT DOCUMENTS 728,821  12/1972  South Africa ....................... 260/514

*Primary Examiner*—Robert Gerstl
*Attorney, Agent, or Firm*—Robert A. Armitage

[57] ABSTRACT

This invention is a group of 8-beta, 12-alpha-PG$_2$ (prostaglandin-type) analogs having variable chain length, or methyl or phenyl substitution in the hydroxy-substituted side-chain, and processes for making them. These compounds are useful for a variety of pharmacological purposes, including anti-ulcer, inhibition of platelet aggregation, increase of nasal patency, and labor inducement at term.

9 Claims, No Drawings

8β,12α,15β-PGE₂ COMPOUNDS

CROSS REFERENCE TO RELATED APPLICATIONS

This is a continuation of application Ser. No. 518,645, filed Oct. 29, 1974 which is a continuation-in-part of my copending application Ser. No. 289,317 filed Sept. 15, 1972, both abandoned.

BACKGROUND OF THE INVENTION

This invention relates to novel compositions of matter, to novel methods for producing those, and to novel chemical intermediates useful in those processes. Particularly, this invention relates to certain novel analogs of prostaglandins $E_2$, $F_{2\alpha}$, and $F_{2\beta}$ in which the configuration at C-8 is beta and at C-12 is alpha, and in which there is variable chain length, or methyl or phenyl substitution in the hydroxy-substituted side-chain.

The known prostaglandins include, for example, prostaglandin $E_2$ (PGE₂), prostaglandin $F_2$ alpha and beta (PGF$_{2\alpha}$ and PGF$_{2\beta}$), and prostaglandin $A_2$ (PGA₂). Each of the above-mentioned known prostaglandins is a derivative of prostanoic acid which has the following structure and atom numbering:

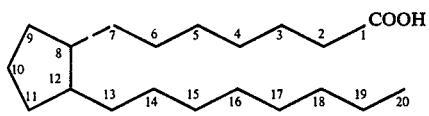

See, for example, Bergstrom et al., Pharmacol. Rev. 20, 1 (1968), and references cited therein. A systematic name for prostanoic acid is 7-([2β-octyl]-cyclopent-1α-yl]-heptanoic acid.

PGE₂ has the following structure:

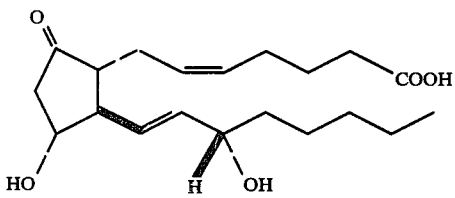

PGF$_{2\alpha}$ has the following structure:

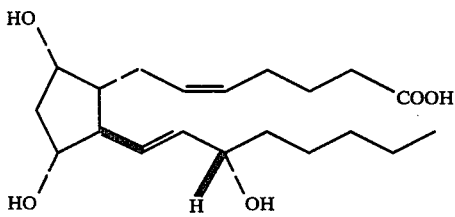

PGF$_{2\beta}$ has the following structure:

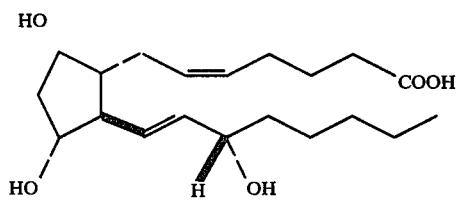

PGA₂ has the following structure:

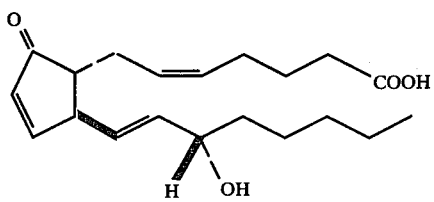

In formulas II to V, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 in formulas II to V is in alpha (S) configuration. See Nature, 212, 38 (1966) for discussion of the stereochemistry of the prostaglandins.

Molecules of the known prostaglandins each have several centers of asymmetry, and can exist in racemic (optically inactive) form and in either of the two enantiomeric (optically active) forms, i.e. the dextrorotatory and levorotatory forms. As drawn, formulas II to V each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. For convenience hereinafter, use of the terms "PGE₂", "PGF$_{2\alpha}$", and the like, will mean the optically active form of that prostaglandin with the same absolute configuration as PGE₂ obtained from mammalian tissues.

PGE₂, PGF$_{2\alpha}$, PGF$_{2\beta}$, and PGA₂, and their esters, acylates, and pharmacologically acceptable salts, are extremely potent in causing various biological responses. For that reason, these compounds are useful for pharmacological purposes. See, for example, Bergstrom et al., cited above. A few of those biological responses are stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE, $PGF_\alpha$, $PGF_\beta$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breating in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc); xanthine derivatives (theophylline and aminophyllin); and corticosteroids (ACTH and prednisolone). Regarding use of these compounds see South African Pat. No. 68/1055.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, $PGF_\alpha$, $PGF_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situation, the intraveneous route of administration is preferred. Doses in the range about 0.005 to about 20 mg. per kg. of body weight per day are used, the exact dose depending on the age, weight, and condition of the patient or animal, and on the frequency and route of administration.

The PGE, $PGF_\alpha$, and $PGF_\beta$ compounds are especially useful as additives to blood, blood products, blood substitutes, and other fluids which are used in artifical extracorporeal circulation and perfusion of isolated body portions, e.g., limbs and organs, whether attached to the original body, detached and being preserved or prepared for transplant, or attached to the new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, $PGE_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephric states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The PGE, $PGF_\alpha$, and $PGF_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, $PGF_\alpha$, and $PGF_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, $PGF_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. Especially for topical use, these prostaglandins are useful in combination with antibiotics, for example, gentamycin, neomycin, polymyxin B, bacitracin, spectinomycin, and oxytetracyline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

SUMMARY OF THE INVENTION

It is a purpose of this invention to provide novel 8-beta, 12-alpha-prostaglandin $E_2$ and $F_2$ analogs. It is a further purpose to provide such analogs having variable chain length, or methyl or phenyl substitution in the hydroxy-substituted side-chain.

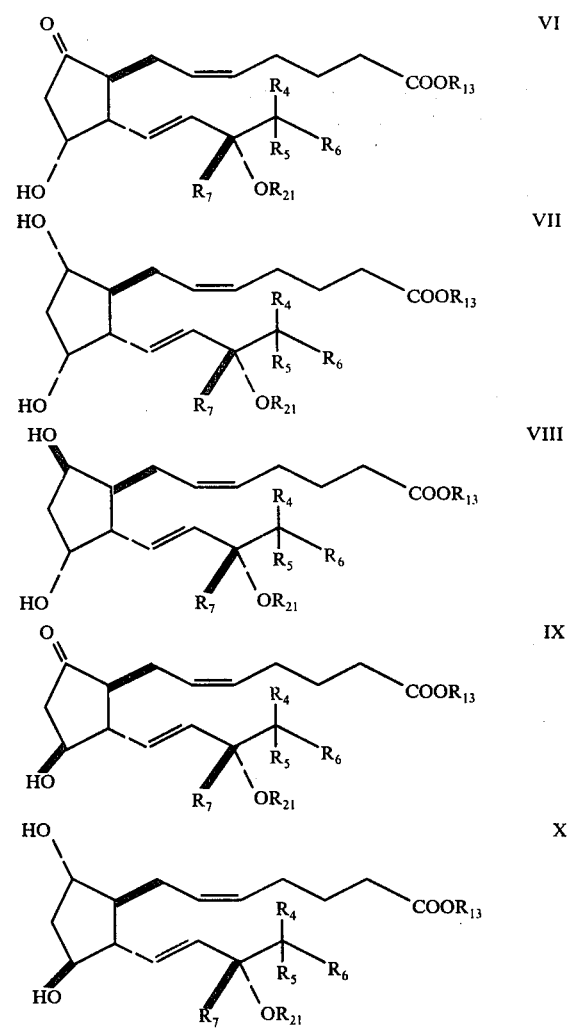

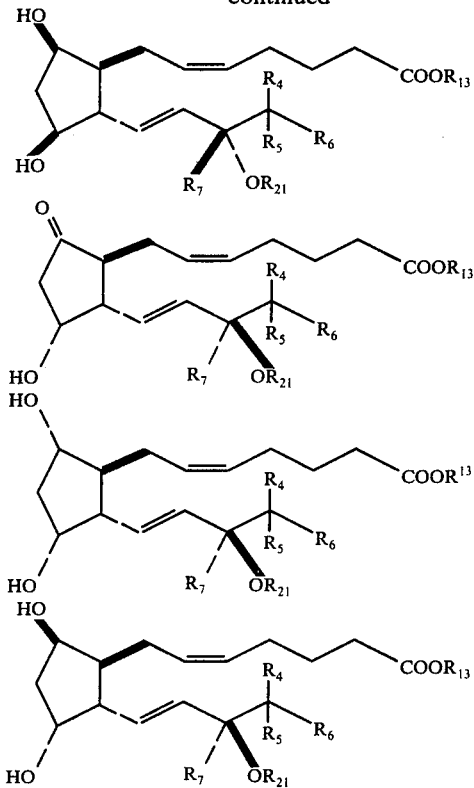

There are also included the alkanoates of 2 to 8 carbon atoms inclusive, and the pharmacologically acceptable salts derived from these compounds when $R_{13}$ is hydrogen.

In formulas VI to XIV, inclusive, $R_4$, $R_5$, and $R_7$ are hydrogen or methyl, being the same or different, $R_6$ is n-butyl or

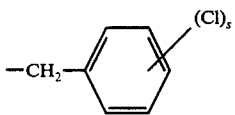

wherein $s$ is zero, one, 2, or 3; $R_{13}$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and $R_{21}$ is hydrogen or alkyl of one to 5 carbon atoms, inclusive.

Formulas VI to XIV represent 8-beta, 12-alpha-prostaglandin E and F type compounds, i.e. analogs of $PGE_2$, $PGF_{2\alpha}$, and $PGF_{2\beta}$ in which the configuration at C-8 is beta rather than alpha as in the natural prostaglandins, and at C-12 is alpha rather than beta. For example, formula VI represents $8\beta,12\alpha$-$PGE_2$ when $R_4$, $R_5$, $R_7$, and $R_{13}$ are hydrogen, and $R_6$ is n-butyl.

Formulas IX to XI represent analogs wherein the hydroxyl at C-11 is in beta configuration rather than in the alpha configuration of the natural prostaglandins. For example, formula X represents $8\beta,9\alpha,11\beta,12\alpha$-$PGF_2$, methyl ester, (alternately "$8\beta,11\beta,12\alpha$-$PGF_2\alpha$, methyl ester") when $R_4$, $R_5$, and $R_7$ are hydrogen, $R_6$ is n-butyl, and $R_{13}$ is methyl.

Formulas XII to XIV represent analogs wherein —$OR_{21}$ at C-15 is in beta configuration rather than in the alpha configuration of the natural prostaglandins. For example, formula XIV represents $8\beta,9\beta,15\beta$-$PGF_2$ when $R_4$, $R_5$, $R_7$, $R_{13}$, and $R_{21}$ are hydrogen, and $R_6$ is n-butyl.

In formulas VI to XIV, when $R_6$ is

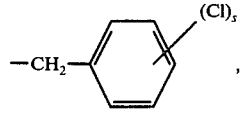

the chain length of the hydroxy-substituted side-chain is 5 carbon atoms plus the terminal phenyl group. For example, Formula VI represents 17-phenyl-18,19,20-trinor-$8\beta,12\alpha$-$PGE_2$ when $R_4$, $R_5$, $R_7$, and $R_{13}$ are hydrogen, and $R_6$ is wherein $s$ is zero, i.e. benzyl. In the name of this formula-VI example, "18,19,20-trinor" indicates absence of three carbon atoms from the hydroxy-substituted side-chain of the $PGE_2$ structure. Following the atom numbering of the prostanoic acid structure, C-18, C-19, and C-20 are construed as missing. The phenyl substitution on C-17, therefore, terminates the side chain.

In formulas VI to XIV, when $R_7$ is methyl, each formula represents a 15-methyl prostaglandin analog. For example, formula VII represents 15-methyl-$8\beta,9\alpha,12\alpha$-$PGF_2$ when $R_4$, $R_5$, and $R_{13}$ are hydrogen, $R_6$ is n-butyl and $R_7$ is methyl.

In formulas VI to XIV, when one or both of $R_4$ and $R_5$ are methyl, a formula represents either 16-methyl or 16,16-dimethyl substitution. For example, formula VIII represents 16-methyl-$8\beta,9\beta,12\alpha$-$PGF_2$ when $R_4$ is methyl, $R_5$, $R_7$, and $R_{13}$ are hydrogen, and $R_6$ is n-butyl; formula IX represents 16,16-dimethyl-$8\beta,11\beta,12\alpha$-$PGE_2$, methyl ester, when $R_4$, $R_5$, and $R_{13}$ are methyl, $R_6$ is n-butyl, and $R_7$ is hydrogen.

With regard to formulas VI to XIV, examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, and 4-chloro-2-methylphenyl.

Accordingly, there is provided an optically active compound of the formula

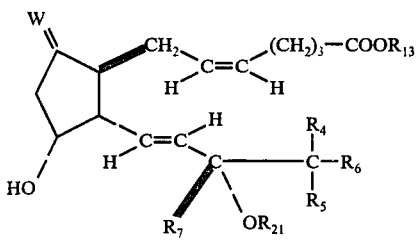   XV wherein $R_4$, $R_5$, and $R_7$ are hydrogen or methyl, being the same or different; wherein $R_6$ is n-butyl or

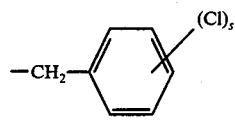

wherein s is zero, one, 2, or 3; wherein $R_{13}$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; $R_{21}$ is hydrogen or alkkyl of one to 5 carbon atoms, inclusive; and wherein W is

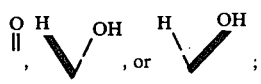

including the lower alkanoates thereof, and the pharmacologically acceptable salts thereof when $R_{13}$ is hydrogen.

Formula XV represents $PGE_2$ analogs when W is

$PGF_{2\alpha}$ analogs when W is

and $PGF_{2\beta}$ analogs when W is

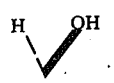

There is also provided an optically active compound of the formula

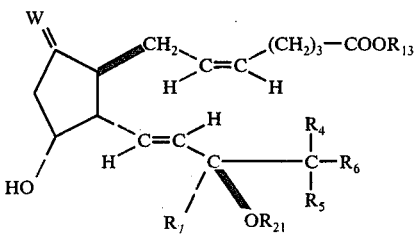   XVI wherein $R_4$, $R_5$, $R_6$, $R_7$, $R_{13}$, $R_{21}$, and W are as defined above.

There is further provided an optically active compound of the formula

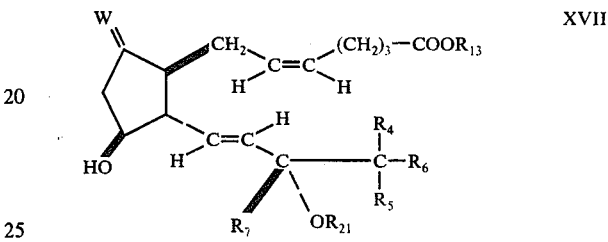   XVII wherein $R_4$, $R_5$, $R_6$, $R_7$, $R_{13}$, $R_{21}$, and W are as defined above, representing the C-11 epimers of formula-XV compounds.

The novel formula VI-to-XVII compounds of this invention each cause the biological responses described above for the PGE, $PGF_\alpha$, $PGF_\beta$, and PGA compounds, respectively, and each of these novel compounds is accordingly useful for the above-described corresponding purposes, and is used for those purposes in the same manner as described above.

The known PGE, $PGF_\alpha$, $PGF_\beta$, and PGA compounds are all potent in causing multiple biological responses even at low doses. For example, $PGE_2$ causes vasodepression and smooth muscle stimulation at the same time it exerts antilipolytic activity. Moreover, for many applications, these known prostaglandins have an inconveniently short duration of biological activity. In striking contrast, the novel prostaglandin analogs of formulas VI to XVII are substantially more specific with regard to potency in causing prostaglandin-like biological responses, and have a substantially longer duration of biological activity. Therefore, each of these novel prostaglandin analogs is surprisingly and unexpectedly more useful than one of the corresponding above-mentioned known prostaglandins for at least one of the pharmacological purposes indicated above for the latter, because it has a different and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

To obtain the optimum combination of biological response specificity, potency, and duration of activity, certain compounds within the scope of formulas VI to XVII are preferred. For example, it is preferred that the hydroxyl at C-15 be in the alpha configuration. It is also preferred that the hydroxyl at C-11 be in the alpha configuration. Another preference is that when $R_7$ is methyl, $R_4$ and $R_5$ are hydrogen. Still another preference is that when $R_6$ is

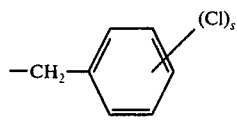

and $s$ is not zero, at least one chloro is in the para position to the methylene attachment to the ring.

Another advantage of the novel compounds of this invention, especially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The $8\beta,12\alpha$ prostaglandin E and F analogs encompassed by formulas VI to XVII including their alkanoates, are used for the purposes described above in the free acid form, in ester form, or in pharmacologically acceptable salt form. When the ester form is used, the ester is any of those within the above definition of $R_{13}$. However, it is preferred that the ester be alkyl of one to 12 carbon atoms, inclusive. Of those alkyl, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of these formula VI-to-XVII compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds encompassed by formulas VI to XVII are used for the purposes described above in free hydroxy form or also in the form wherein the hydroxy moieties are transformed to lower alkanoate moieties, e.g., —OH to —OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of formulas VI to XVII are administered in various ways for various purposes; e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_{13}$ in the formula VI-to-XVII compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers, are used for oral sublingual administration. For rectal or vaginal administration, suppositories prepared as known in the art are used. For tissue implants, a sterile tablet or silicone rubber capsule or other object containing or impregnated with the substance is used.

The $8\beta,12\alpha$-prostaglandin $E_2$ and $F_2$ analogs encompassed by formulas VI through XVII are produced by the reactions and procedures described and exemplified hereinafter.

Reference to Charts A, B, C, and D herein will make clear the process steps. In Chart A is shown the transformation of the starting material containing an anion of the formula

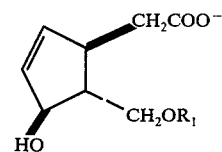     XVIII

CHART A

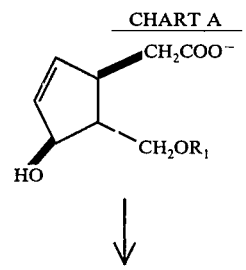     XVIII

-continued
CHART A
XIX
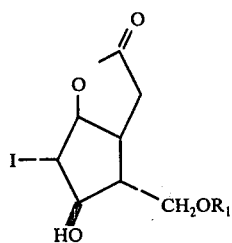
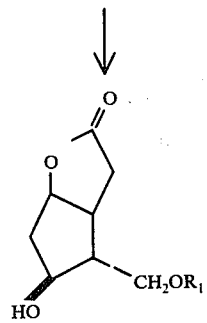
XX
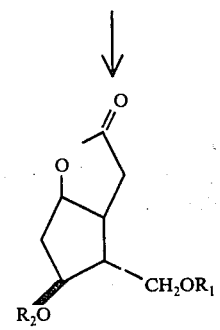
XXI
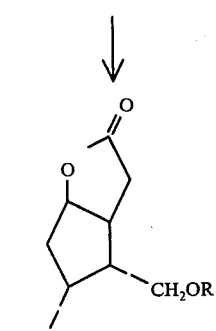
XXII
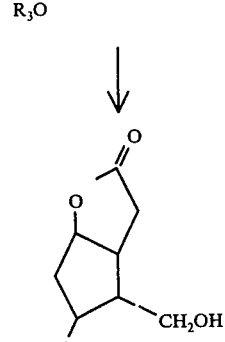
XXIII
-continued
CHART A
XXIV
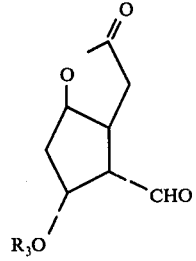
XXV
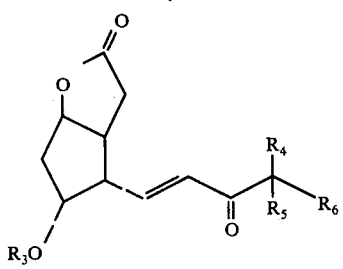
XXVI
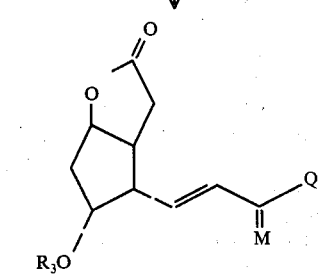
XXVII
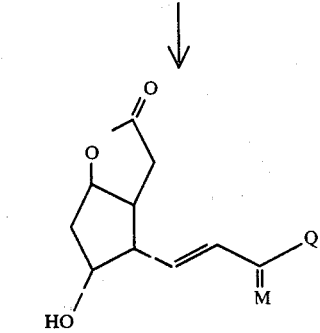
XXVIII
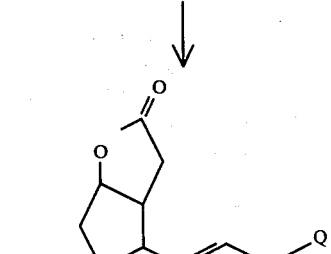
wherein $R_1$ is methyl or benzyl to a key intermediate

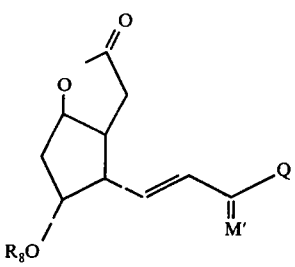

wherein M' is

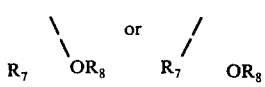

wherein $R_8$ is hydrogen or a blocking group Z, as defined hereinafter, and wherein Q is

wherein $R_4$, $R_5$, and $R_6$ are as defined above. The starting material is readily available. See E. J. Corey et al., J. Am. Chem. Soc. 92, 397 (1970) describing the resolution of XVIII with (—)-ephedrine.

Iodolactone XIX is obtained by methods known in the art, e.g. treatment of the sodium salt of XVIII in water with potassium triiodide. The formula-XX compound is obtained by deiodination of XIX using a reagent which does not react with the lactone ring, e.g. zinc dust, sodium hydride, hydrogen-palladium, hydrogen and Raney nickel or platinum, and the like. Especially preferred is tributyltin hydride in benzene at about 5° C. with 2,2'-azobis-(2-methylpropionitrile) as initiator.

Compound XXI is obtained by reacting the formula-XX compound with a hydrocarbonsulfonyl or halohydrocarbonsulfonyl chloride or bromide, preferably a lower alkanesulfonyl chloride or bromide, especially methanesulfonyl chloride, or a benzene- or substituted-benzenesulfonyl chloride or bromide, e.g. 2-bromobenzenesulfonyl chloride or p-toluenesulfonyl chloride. This reaction is done in the presence of a sufficient amount of tertiary amine, e.g. triethylamine or pyridine, to absorb the hydrogen chloride or hydrogen bromide by-product, and at a low temperature, preferably not over 30° C.

Inversion from beta configuration at the 3-position of the formula-XXI lactone to the alpha configuration at the 3-position of the formula-XXII lactone is achieved by reaction of the formula-XXI sulfonate with an alkali metal salt of an aliphatic acid, preferably lower aliphatic of one to 8 carbon atoms, especially acetic acid, or an aromatic acid, including benzoic, substituted benzoic, monoesterified phthalic or its isomers, naphthoic, and substituted naphthoic. This reaction is done in an organic liquid medium such as dimethyl sulfoxide in the range of 50°–100° C. At about 85° C. the reaction is complete in 3–4 hours, resulting in inversion and replacement at the 3-position of the sulfonate moiety by $R_3$, defined herein as (a)

XXVIII

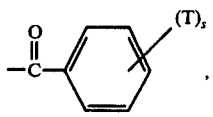

wherein T is alkyl of one to 4 carbon atoms, Inclusive, phenylalkyl of 7 to 10 carbon atoms, inclusive, or nitro, and $s$ is zero to 5, inclusive, provided that not more than two T's are other than alkyl, and that the total number of carbon atoms in the T's does not exceed 10 carbon atoms; (b)

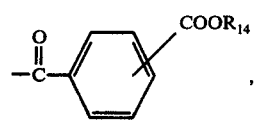

wherein $R_{14}$ is alkyl of one to 4 carbon atoms inclusive; (c)

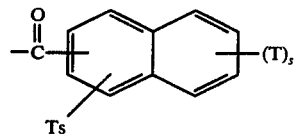

wherein T and $s$ are as defined above; or (d) acetyl.

Examples of $R_3$ are benzoyl, substituted benzoyl, e.g. (2-, 3- or 4-)methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)toluyl, 2-, 3-, or 4-phenethylbenzoyl, 2-, 3-, or 4-nitrobenzoyl, (2,4-, 2,5-, or 3,5-)dinitrobenzoyl, 3,4-dimethyl-2-nitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

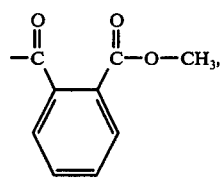

isophthaloyl, e.g.

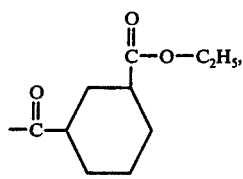

or terephthaloyl, e.g.

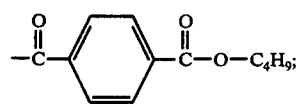

(1- or 2-)naphthoyl; and substituted naphthoyl, e.g. (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5- or 8-)nitro-1-naphthoyl, 4,5-dinitro-1-naphthoyl, (3-, 4-, 6-, 7- or 8-)methyl-1-naphthoyl, 4-ethyl-2-naphthoyl, and (5- or 8-)nitro-2-naphthoyl.

The formula-XXIII compound is obtained by demethylation (or debenzylation) of XXII with a reagent that does not attack the $OR_3$ moiety, for example, boron tribromide or trichloride. The reaction is carried out preferably in an inert solvent at about 0°–5° C.

The formula-XXIV compound is obtained by oxidation of the —$CH_2OH$ of XXIII to —CHO, avoiding decomposition of the lactone ring. Useful for this purpose are dichromatesulfuric acid, Jones' reagent, or lead tetraacetate. Especially preferred is Collins' reagent (pyridine-$C\gamma O_3$) at about 0°–10° C.

The formula-XXV compound is obtained by Wittig alkylation of XXIV, using a ylide consisting of a phosphonate anion of the formula

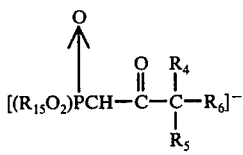    LV wherein $R_{15}$ is alkyl of one to 8 carbon atoms, inclusive, and $R_4$, $R_5$, and $R_6$ are as defined above. The trans enone lactone is obtained stereospecifically (see D. H. Wadsworth et al., J. Org. Chem. 30, 680 (1965)).

The phosphonates are available or prepared by methods known in the art, e.g. by reaction of a dialkyl methylphosphonate with an ethyl ester of an appropriate aliphatic acid or phenyl-substituted aliphatic acid.

The formula-XXVI compound, wherein M is

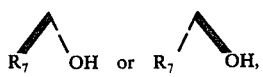

wherein $R_7$ is hydrogen and wherein Q is as defined above, is obtained as a mixture of the alpha and beta isomers with respect to M, by reduction of XXV. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy) aluminum hydride, metal trialkoxy borohydrides, e.g., sodium trimethoxyborohydride, lithium borohydride, diisobutyl aluminum hydride. The alpha and beta isomers are separated by chromatography, e.g. silica gel chromatography or high pressure liquid chromatography. See, for example, "Modern Practice of Liquid Chromatography", J. J. Kirkland, ed., Wiley-Interscience, 1971.

The formula-XXVII compound is obtained, if desired, by deacylation of XXVI with an alkali metal carbonate, for example potassium carbonate in methanol at about 25° C. Thereafter, compound XXVII may be used directly in the steps shown in Chart B, in which case XXVII is identical with XXVIII. Alternately, compound XXVIII of Charts A and B

CHART B

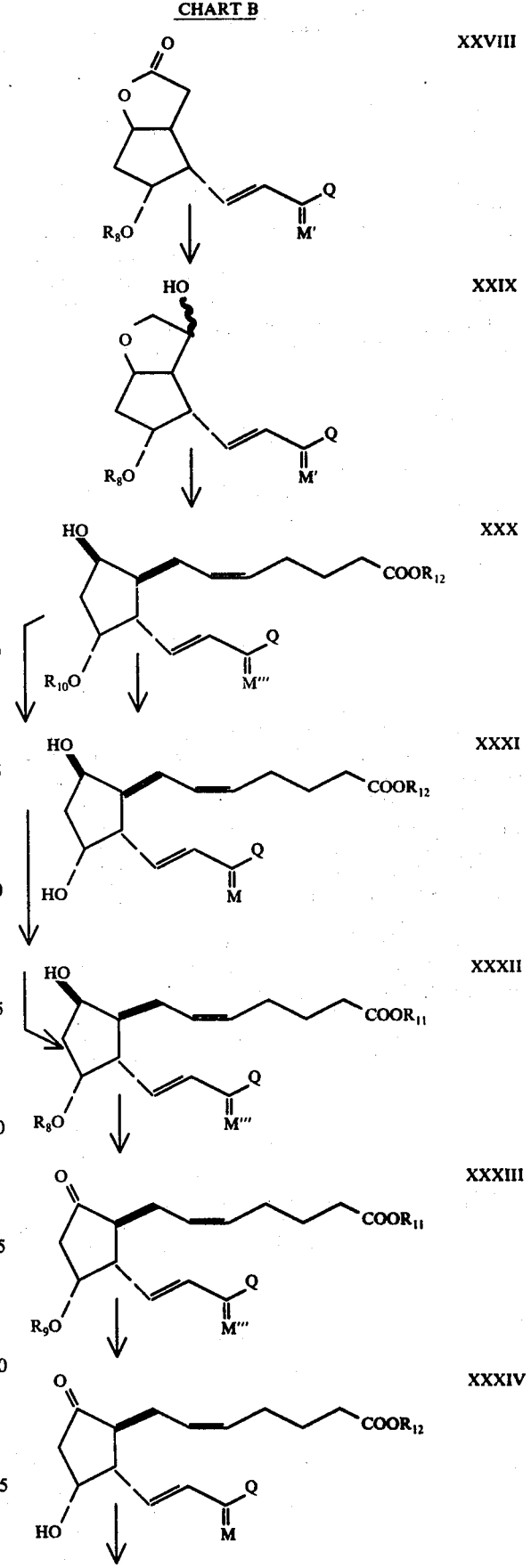

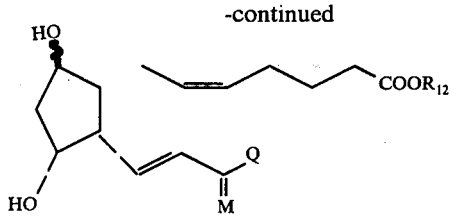

XXXV is made by replacing hydrogen atoms on all hydroxy is with a blocking group Z.

The blocking group, Z, is any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products.

Several blocking groups are known in the art, e.g. tetrahydropyranyl, acetyl, and p-phenylbenzoyl (see Corey et al., J. Am. Chem. Soc. 93, 1491 (1971)).

Those which have been found useful include (a) carboxyacyl within the scope of $R_3$, defined above, i.e. acetyl, benzoyl, naphthoyl, and the like; (b) tetrahydropyranyl; (c) tetrahydrofuranyl; (d) a group of the formula

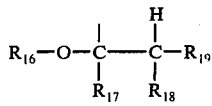

wherein $R_{16}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{17}$ and $R_{18}$ are the same or different, being hydrogen, alkyl of one to 4 carbon atoms, inclusive, phenyl or phenyl substituted with one, 2, or 3 alkyl of one to 4 carbon atoms, inclusive, or, when $R_{17}$ and $R_{18}$ are taken together, —$(CH_2)a$— or —$(CH_2)b$—O—$(CH_2)c$— wherein $a$ is 3, 4, or 5, $b$ is one, 2, or 3, and $c$ is one, 2, or 3 with the proviso that $b$ plus c is 2, 3, or 4, and wherein $R_{18}$ is hydrogen or phenyl; or (e) -Si(A)$_3$ wherein A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive.

It is desirable that the formula-XXVIII intermediate have a blocking group Z at $R_8$, although that is not essential. It is preferred, however, that intermediate XXXII (Chart B) have a blocking group at $R_9$, and for this purpose $R_9$ includes the blocking groups of $R_8$ but without the carboxyacyl groups. It is evident, therefore, that if intermediate XXXII is to be made, it is advantageous to prepare XXVIII with either the ether-linked blocking group of types (b), (c) or (d) above, or the silyl of type (e).

In replacing the hydrogen atoms of the hydroxyl groups with a carboxyacyl blocking group, methods known in the art are used. Thus, for example, benzoic anhydride is reacted with the formula-XXVII compound in the presence of pyridine.

Preferably, however, an acyl halide, for example, benzoyl chloride, is reacted with the formula-XXVII compound in the presence of a tertiary amine such as pyridine, triethylamine, and the like. The reaction is carried out under a variety of conditions using procedures generally known in the art. Generally, mild conditions are employed, e.g. 20°-60° C., contacting the reactants in a liquid medium, e.g. excess pyridine or an inert solvent such as benzene, toluene, or chloroform. The acylating agent is used either in stoichiometric amount or in excess. If the acyl chloride is not available, it is made from the corresponding acid and phosphorus pentachloride as is known in the art.

When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°-50° C.

When the blocking group is of the formula

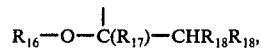

as defined above, the appropriate reagent is a vinyl ether, e.g. isobutyl vinyl ether or any vinyl ether of the formula $R_{16}$—O—C($R_{17}$)=$CR_{18}R_{19}$ wherein $R_{16}$, $R_{17}$, $R_{18}$, and $R_{19}$ are as defined above; or an unsaturated cyclic or heterocyclic compound, e.g. 1-cyclohex-1-yl methyl ether

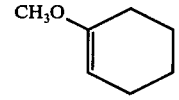

or 5,6-dihydro-4-methoxy-2H-pyran

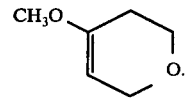

See C. B. Reese et al., J. Am. Chem. Soc. 89, 3366 (1967). The reaction conditions for such vinyl ethers and unsaturates are similar to those for dihydropyran above.

When the blocking group is silyl of the formula —Si(A)$_3$, the formula-XXVII compound is transformed to a silyl derivative of formula XXVIII by procedures known in the art. See, for example, Pierce, "Silylation of Organic Compounds," Pierce Chemical Co., Rockford, Illinois (1968). The necessary silylating agents for these transformations are known in the art or are prepared by methods known in the art. See, for example, Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstituted mono- chlorosilanes suitable for this purpose include chlorotrimethylsilane, chlorotriisobutylsilane, chlorotriphenylsilane, chlorotris(p-chlorophenyl)silane, chlorotrim-tolylsilane, and tribenzylchlorosilane. Alternately, a chlorosilane is used with a corresponding disilazane. Examples of other silylating agents suitable for forming the formula-XXVIII intermediates include pentamethylsilylamine, pentaethylsilylamine, N-trimethylsilyldiethylamine, 1,1,1-triethyl-N,N-dimethylsilylamine, N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

Continuing with Chart B, there are shown the steps by which intermediate XXVIII is transformed to PGE analogs of formula XXXIV and to PGF analogs of formulas XXXI and XXXV. In Chart B, M''' is

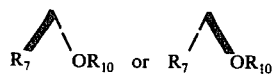

wherein $R_{10}$ is (a) hydrogen; (b) tetrahydropyranyl; (c) tetrahydrofuranyl; (d) a group of the formula

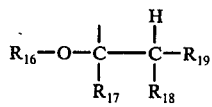

wherein $R_{16}$, $R_{17}$, $R_{18}$, and $R_{19}$ are as defined above; or (e) —Si(A)$_3$ wherein A is as defined above. Also in Chart B, $R_{11}$ is hydrogen, methyl, or —Si(A)$_3$ wherein A is as defined above; $R_{12}$ is hydrogen or methyl; ~ indicates attachment of hydroxyl in alpha or beta configuration; and M, M', Q, $R_8$ and $R_9$ are as defined above.

Lactol XXIX is obtained on reduction of the formula-XXVIII lactone without reducing the 13,14-ethylenic group. For this purpose, diisobutylaluminum hydride is used. The reduction is preferably done at −60 to −78° C.

The formula-XXX compound is obtained from lactol XXIX by the Wittig reaction, using a Wittig reagent derived from 4-carboxybutyltriphenylphosphonium bromide, HOOC-(CH$_2$)$_4$-P(C$_6$H$_5$)$_3$Br, and sodio dimethylsulfinylcarbanide. See E. J. Corey et al., J. Am. Chem. Soc. 91, 5675 (1969). The reaction is conveniently carried out at about 25° C. This formula-XXX compound serves as an intermediate for preparing either the PGF$_2\beta$ analog XXXI or the PGE$_2$ analog XXXIV. The latter may serve as an intermediate for the preparation of PGF$_2\alpha$ analog XXXV, wherein ~ is alpha.

The formula-XXXI PGF$_2\beta$-type product is obtained on hydrolysis of any blocking groups at $R_{10}$, e.g. tetrahydropyranyl or silyl groups. For this purpose, the formula-XXX compound is contacted with methanol-HCl or with acetic acid/water/tetrahydrofuran at 40°-55° C. Specifically for the silyl groups, milder conditions may be employed. See Pierce, cited above, especially p, 447 thereof. A mixture of water and sufficient of a water-miscible organic diluent to give a homogeneous hydrolysis reaction mixture represents a suitable reaction medium. Addition of a catalytic amount of an organic or inorganic acid hastens the hydrolysis. The length of time required for the hydrolysis is determined in part by the hydrolysis temperature. With a mixture of water and methanol at 25° C., several hours is usually sufficient for hydrolysis. At 0° C., several days is usually necessary.

The formula-XXXIV PGE$_2$-type product is obtained by first transforming the formula-XXX intermediate to intermediate XXXII having a blocking group $R_8$, by one of the methods described above. When $R_7$ at C-15 by compound XXX is hydrogen, the hydrogen on the C-15 hydroxyl is also replaced by a blocking group in the above reaction. When $R_7$ is methyl, it is immaterial whether M''' contains a free hydroxyl or a blocking group, since the tertiary hydroxyl at C-15 is less susceptible to oxidation than the secondary hydroxyl at C-9 in the subsequent step. When silylation is employed and $R_{12}$ in the formula-XXX intermediate is hydrogen, the —COOH moiety thereby defined is simultaneously transformed to —COO—Si—(A)$_3$, additional silylating agent being used for this purpose. It is immaterial whether $R_{12}$ is completely silylated or not for the purposes of Chart B, so that $R_{11}$ may be all or partially hydrogen.

Successive steps in Chart B relate to the transformation of intermediate XXXII to a PGE$_2$-type product by (1) oxidizing intermediate XXXII at the 9-hydroxy position by known methods, e.g. with Jones or Collins reagent, and (2) replacing the blocking groups at $R_9$, $R_{10}$, and $R_{11}$ with hydrogen, i.e. by hydrolysis as discussed above for removal of tetrahydropyranyl or silyl groups.

The formula-XXXV PGF$_2\alpha$ analog wherein ~ is alpha is made from the formula-XXXIV PGE$_2$ analog by reduction of the carbonyl at C-9 by methods known in the art. See, for example, Bergstrom et al., Arkiv Kemi 19, 563 (1963), Acta. Chem. Scand. 16, 969 (1962), and British Specification No. 1,097,533. Any reducing agent is used which does not react with carbon-carbon double bonds or ester groups. Preferred reagents are lithium(tri-tert-butoxy)aluminum hydride, the metal borohydrides, especially sodium, potassium and zinc borohydrides, the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964), Especially preferred as separation methods are partition chromatographic procedures, both normal and reversed phase, preparative thin layer chromatography, and countercurrent distribution procedures.

As stated above, the C-15 epimers may be separated at the formula-XXVI stage, in which case they are subjected to the successive steps of Charts A and B individually. They may also be separated at any later stage in Chart A or B, or if desired, left together as a mixture.

In Charts C and D are shown the steps by which the 11$\beta$ analogs of this invention are prepared. The reactions whereby starting material XX is transformed to intermediate XLIV are substantially as described herein for Charts A and B, with the exception of the C-11 isomerization of Chart A employing the sulfonate-carboxylate transformation from formula XXI to formula XXII. This isomerization is, of course, not used where the products of Chart C retain the configuration of starting material XX.

In Chart C are shown intermediates XLIV and XLV which are readily transformed to the respective 8β,9β,11β,12α-PGF$_2$ and 8β,11β,12α-PGE$_2$ analogs by methods known in the art or
CHART C
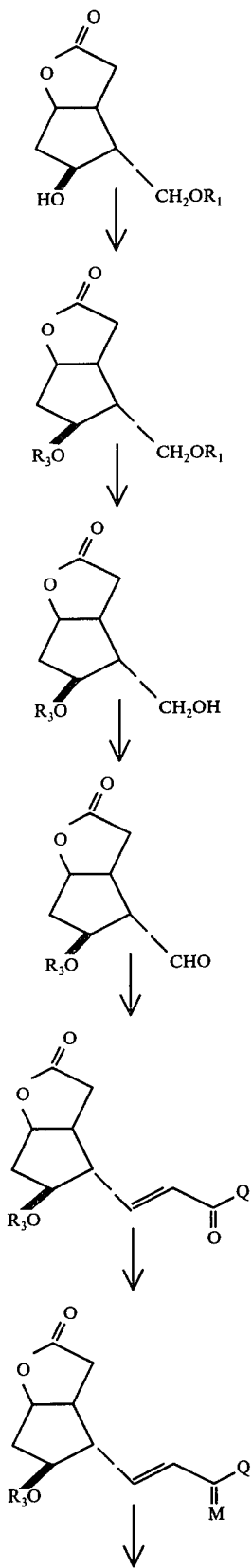
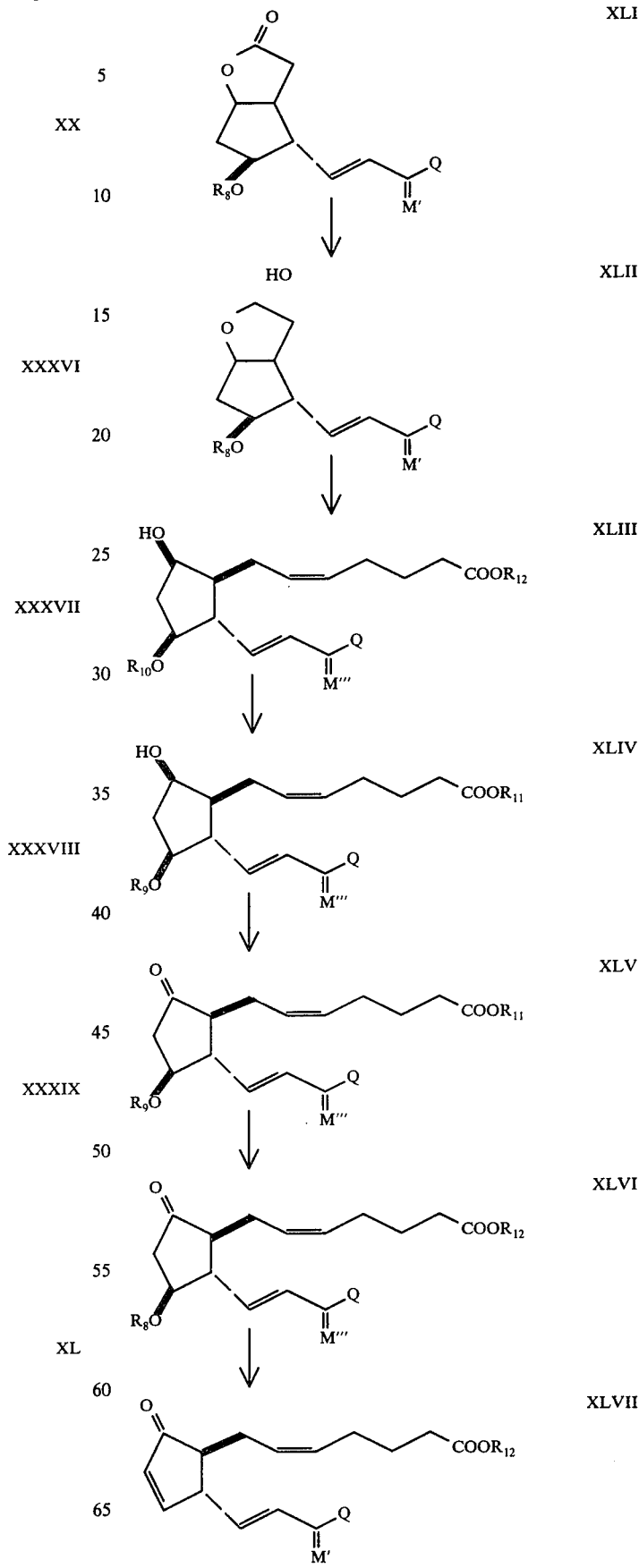

CHART D

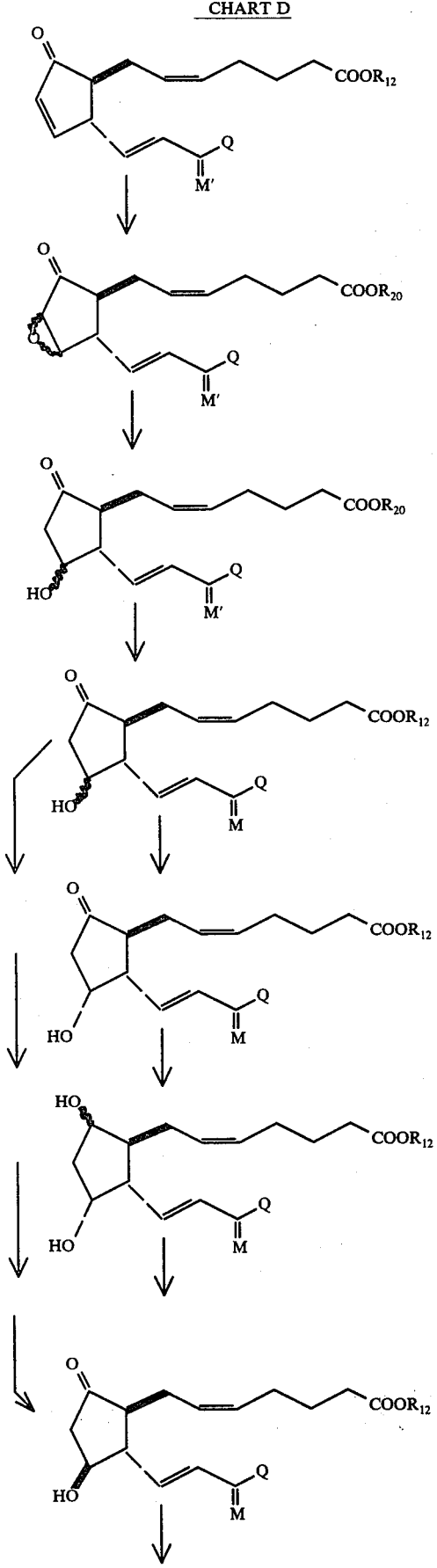

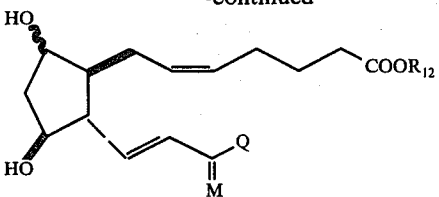

described herein.

The chromatographic separation of the C-15 epimers of the 15-methyl analogs is readily, and in fact preferably, effected on intermediate XLIII, thereafter carrying forward the individual 15α and 15β epimers through the sequential steps of Charts C and D. Those C-15 epimers wherein $R_7$ is hydrogen are separable at the formula-XL stage or any subsequent stage, thereafter being subjected to the successive steps of Charts C or D individually. The separation is readily achieved by methods described herein, for example silica gel chromatography.

In Chart C is also shown the transformation of a $PGE_2$-type compound to a $PGA_2$ analog. For this purpose intermediate XLVI is subjected to acid dehydration, using methods known in the art. See, for example, Pike et al., Proc. Nobel Symposium II, Stockholm (1966), Interscience Publishers, New York, pp. 162–163 (1967); and British Specification 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

Alternately when $R_7$ is methyl, and preferably when $R_8$ is acetyl, compound XLVI is contacted with potassium acetate in solution, e.g. in methanol. The reaction proceeds smoothly at about 20°–30° C. and is substantially free of side reactions.

The formula-XLVII $PGA_2$ analogs are useful compounds not only for their prostaglandin-like properties discussed above, but as intermediates for preparing the 11α $PG_2$ analogs of this invention and the C-9 epimers of the $PGF_2$ analogs according to the steps of Chart D.

In Chart D are shown the transformations of the formula-XLVII $PGA_2$ analog to the formula LI, LII, LIII, and LIV analogs, using methods known in the art. See, for example, G. L. Bundy et al., J. Am. Chem. Soc. 94, 2123 (1972). There are first formed the formula-XLVIII 10,11-epoxides, using any agent known to epoxidize an α,β-unsaturated ketone without reacting with isolated carboncarbon double bonds, for example see Steroid Reactions, Carl Djerassi, ed., Holden-Day Inc., 1963, p. 593. Especially preferred are aqueous hydrogen peroxide or an organic tertiary hydroperoxide. See, for example, Organic Peroxides, A. V. Tobolsky et al., Interscience Publishers, N.Y., 1954. For this purpose, the peroxide or hydroperoxide is employed in an amount of at least one equivalent per mole of Formula-XLVII reactant in the presence of a strong base, e.g., an alkali metal hydroxide, a metal alkoxide, or a quaternary ammonium hydroxide. For example, there is employed lithium hydroxide, sodium hydroxide, potassium hydroxide, lithium ethoxide, lithium octyloxide, magnesium methoxide, magnesium isopropoxide, benzyltrimethylammonium hydroxide, and the like.

It is advantageous to use an inert liquid diluent in the epoxidation step to produce a mobile homogenous reaction mixture, for example, a lower alkanol, dioxane, tetrahydrofuran, dimethoxyethane, dimethylsulfoxide, or dimethylsulfone. A reaction temperature in the range −60° to 0° C. is generally preferred, especially below −10° C. At a temperature of −20° C., the epoxidation is usually complete in 3 to 6 hours. It is also preferred that the reaction be carried out in an atmosphere of an inert gas, e.g., nitrogen, helium, or argon. When the reaction is complete as shown by the absence of starting material on TLC plates (5% acetone in dichloromethane), the reaction mixture is neutralized, and the epoxy product is isolated by procedures known in the art, for example, evaporation of the diluent and extraction of the residue with an appropriate water-immiscible solvent, e.g., ethyl acetate.

This transformation of XLVII to XLVIII usually produces a mixture of formula-XLVIII alpha and beta epoxides. Although these mixtures are separable into the individual alpha and beta isomers, for example, by chromatography by procedures known to be useful for separating alpha and beta epoxide mixtures, it is usually advantageous to transform the formula-XLVIII mixture of alpha and beta epoxides to the corresponding mixture of formula-XLIX 11α and 11β hydroxy compounds. The latter mixture is then readily separated into the 11α and 11β compounds, for example, by chromatography on silica gel.

Referring again to Chart D, the transformation of epoxide XLVIII to hydroxy compound XLIX is accomplished by reduction with chromium (II) salts, e.g., chromium (II) chloride or chromium (II) acetate. Those salts are prepared by methods known in the art, e.g., Inorganic Syntheses, VIII, 125 (1966); ibid., VI, 144 (1960); ibid. III, 148 (1950); ibid. I, 122 (1939); and references cited in those. This reduction is carried out by procedures known in the art for using chromium (II) salts to reduce epoxides of αβ-unsaturated ketones to β-hydroxy ketones. See, for example, Cole et al., J. Org. Chem. 19, 131 (1954), and Neher et al., Helv. Chem. Acta 42, 132 (1959). In these reactions, the absence of air and strong acids is desirable.

Amalgamated aluminum metal has also been found to be useful as a reducing agent in place of chromium (II) salts for the above purpose. Amalgamated aluminum is prepared by procedures known in the art, for example, by contacting aluminum metal in the form of foil, thin sheet, turnings, or granules with a mercury (II) salt, for example, mercuric chloride, advantageously in the presence of sufficient water to dissolve the mercury (II) salt. Preferably, the surface of the aluminum metal is free of oxide. That is readily accomplished by physical removal of the usual oxide layer, e.g., by abrasion or scraping, or chemically, e.g., by etching with aqueous sodium hydroxide solution. It is only necessary that the aluminum surface be amalgamated. The amalgamated aluminum should be freshly prepared, and maintained in the absence of air and moisture until used.

The reductive opening of the formula-XLVIII epoxide ring is accomplished by contacting said epoxide with the amalgamated aluminum in the presence of a hydroxylic solvent and sufficient inert organic liquid diluent to give a mobile and homogeneous reaction mixture with respect to the hydroxylic solvent and said epoxide. Among hydroxylic solvents, water is especially preferred although lower alkanols, e.g., methanol and ethanols are also operable.

Examples of inert organic liquid diluents are normally liquid ethers such as diethyl ether, tetrahydrofuran, dimethoxyethane, diglyme (dimethyl ether of diethylene glycol), and the like. Especially preferred is tetrahydrofuran. When a water-immiscible liquid diluent is used, a mixture of water and methanol or ethanol is especially useful in this reaction since the latter two solvents also aid in forming the desired homogeneous reaction mixture. For example, a mixture of diethyl ether and water is used with sufficient methanol to give a homogeneous reaction mixture.

As a modification of the above-described process for reductive opening of the epoxide, it has been found that instead of employing a formula-XLVIII compound wherein $R_{20}$ is hydrogen, the reductive opening reaction proceeds more smoothly and completely if there is used, instead, an epoxide wherein $R_{20}$ is either methyl or a cation of an alkali or alkaline earth metal or a quaternary ammonium group.

Thus, a free acid formula-XLVIII epoxide compound is treated with a hydroxide or oxide of lithium, sodium, potassium, magnesium, calcium, barium, or strontium prior to contacting with the aluminum amalgam. Optionally, the quaternary ammonium bases are used for this neutralization, for example benzyltrimethylammonium hydroxide. By using the above-described salts, the reduction step proceeds smoothly without formation of insoluble aluminum salts which hinder the reaction. Following the reduction or hydrolysis step, the $R_{20}$ cations are replaced with hydrogen by means known in the art, for example by acidification and extraction of the acid compound into an organic phase, to form the formula-L compound.

The separate C-11 epimers of formula LI and LIII, $PGE_2$ analogs within the scope of this invention, are useful prostaglandin analogs for the purposes discussed above. They may also be transformed to the corresponding $PGF_2$ analogs of formula LII and LIV, respectively, by methods known in the art or described herein.

The 15-alkyl ether prostaglandin-type compounds included within formulas VI to XIV are produced by the sequence of reactions illustrated in Charts E, F, and G. In general, by these methods, the 15-alkyl ether group is introduced into the bicyclic lactone intermediates XXVI (Chart A) and XL (Chart C) prior to the lactol formation and Wittig reaction for forming the carboxy side chain. Alternatively, the 15-alkyl ether compounds are prepared by alkylation of a suitably blocked prostaglandin-type compound. See Belg. Pat. No. 783,028, Nov. 6, 1972; Netherlands Application No. 7205997, Derwent Farmdoc 74818 T.

Referring to Chart E, starting material XXVI is available by the processes of Chart A, discussed above. In Chart E, M, Q, $R_3$, $R_8$, $R_9$, $R_{10}$, $R_{11}$, and $R_{12}$ have the same meanings as in Charts A and B; $M^{1v}$ is defined as

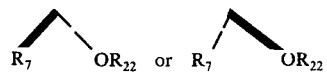

wherein $R_7$ is hydrogen or methyl and $R_{22}$ is alkyl of one to 5 carbon atoms, inclusive.

The formula-LVI compound is prepared by alkylation of the side-chain hydroxy of the formula-XXVI compound thereby replacing hydroxy with the $-OR_{22}$ moiety. For this purpose, diazoalkanes may be employed, preferably in the
CHART E
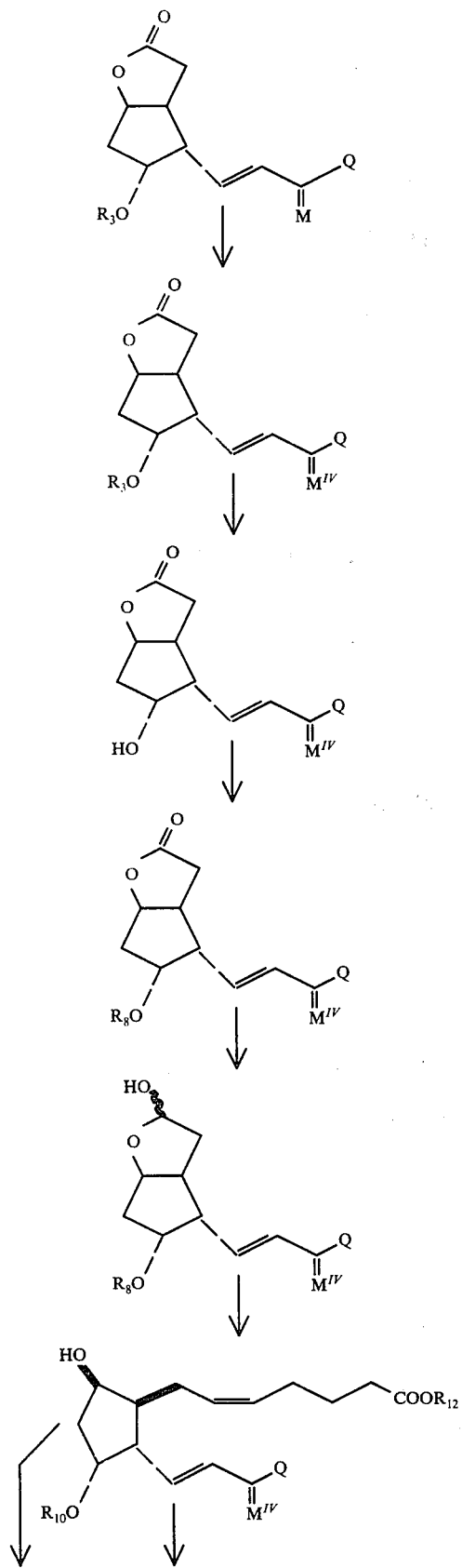
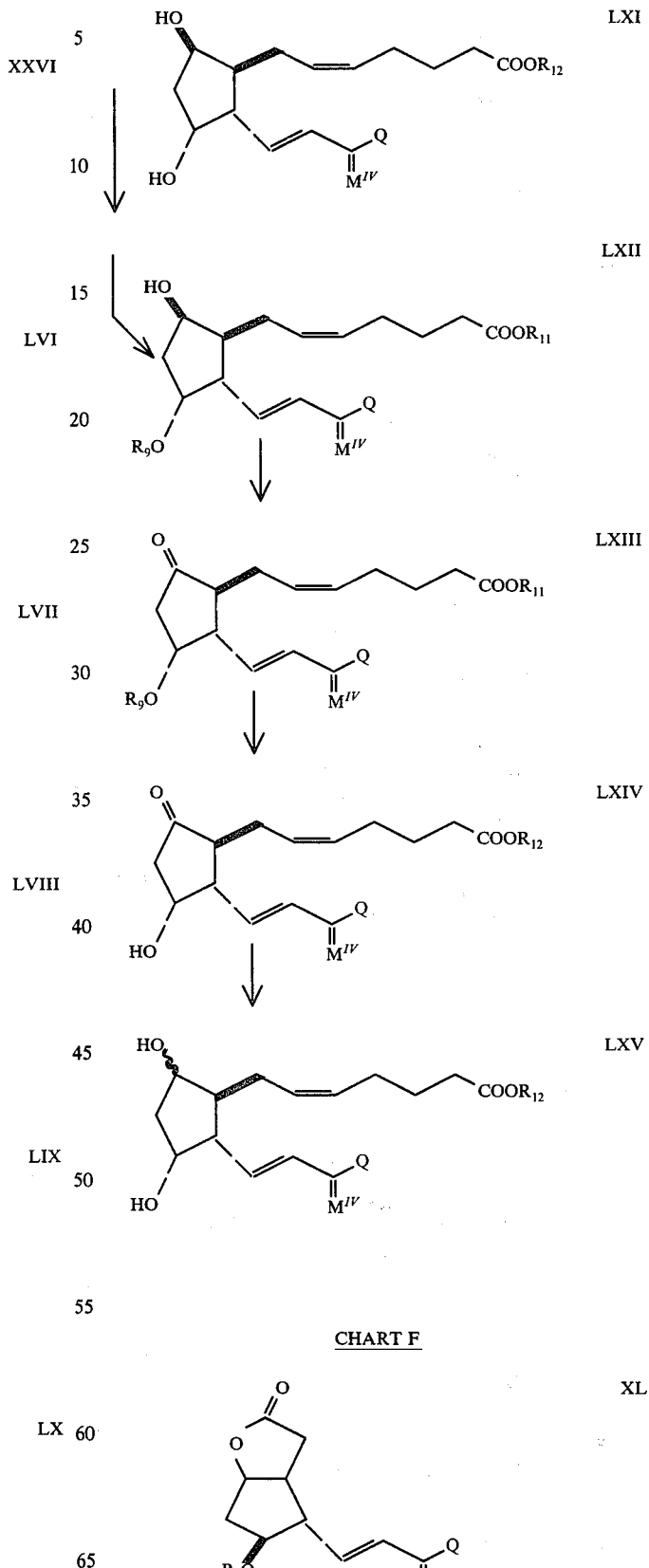
CHART F
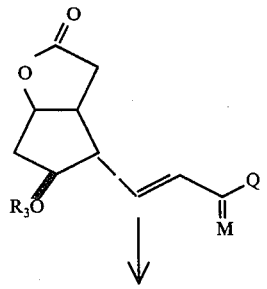

-continued
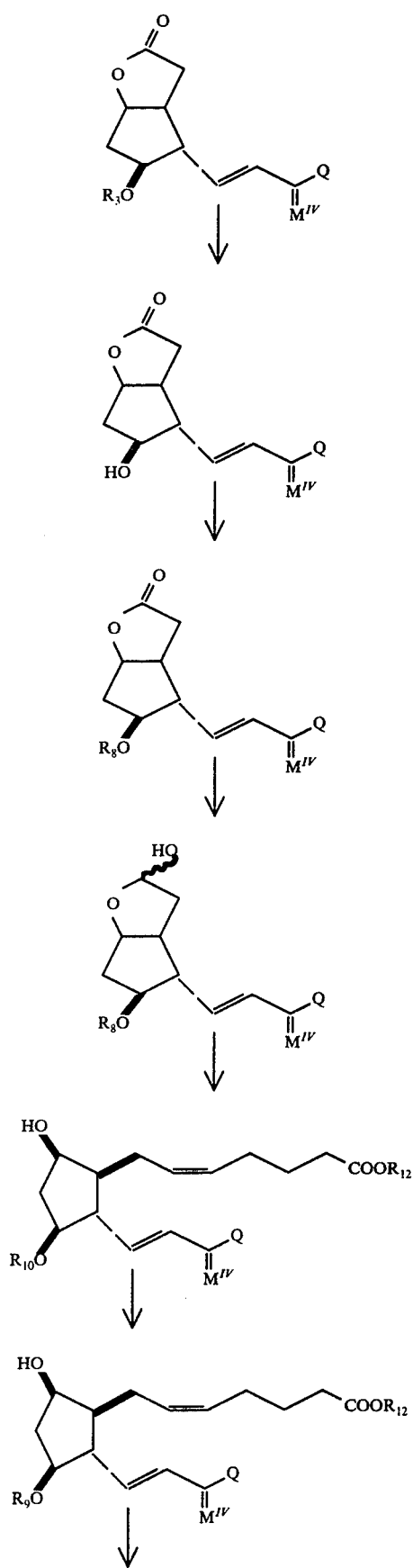
-continued
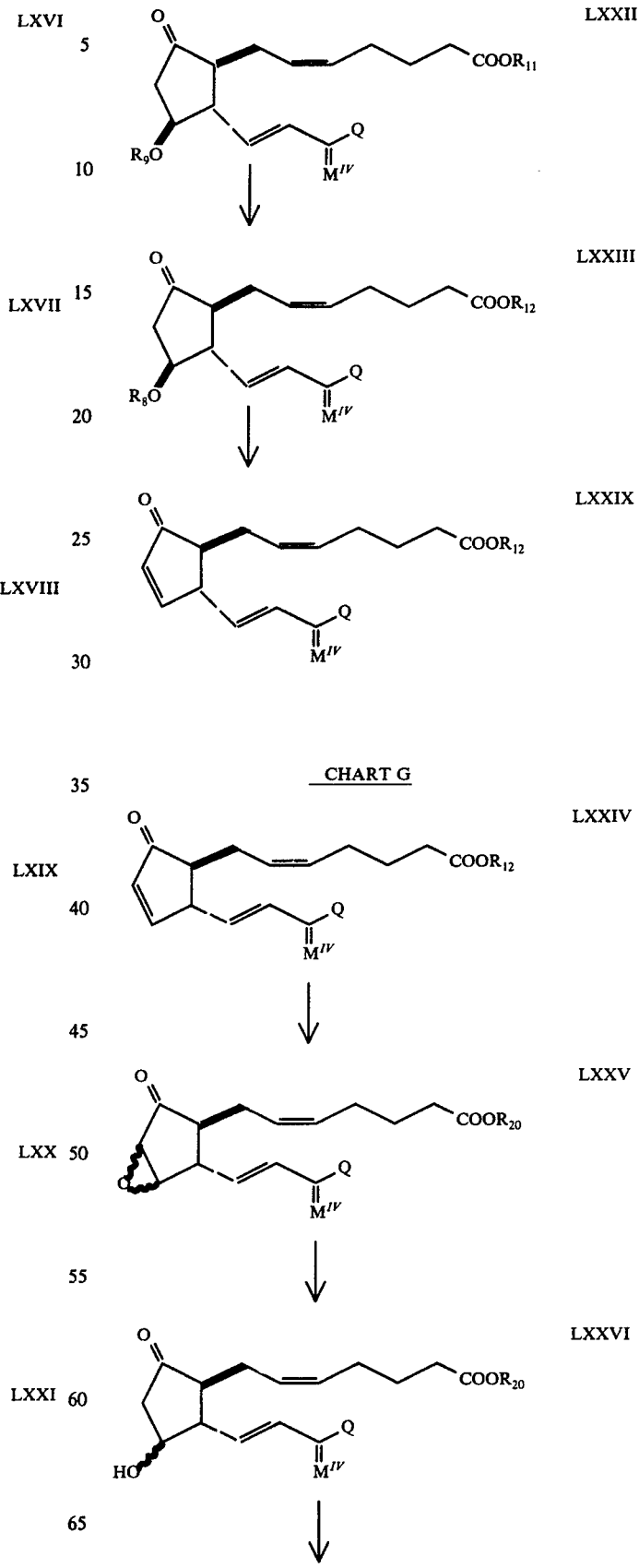
CHART G

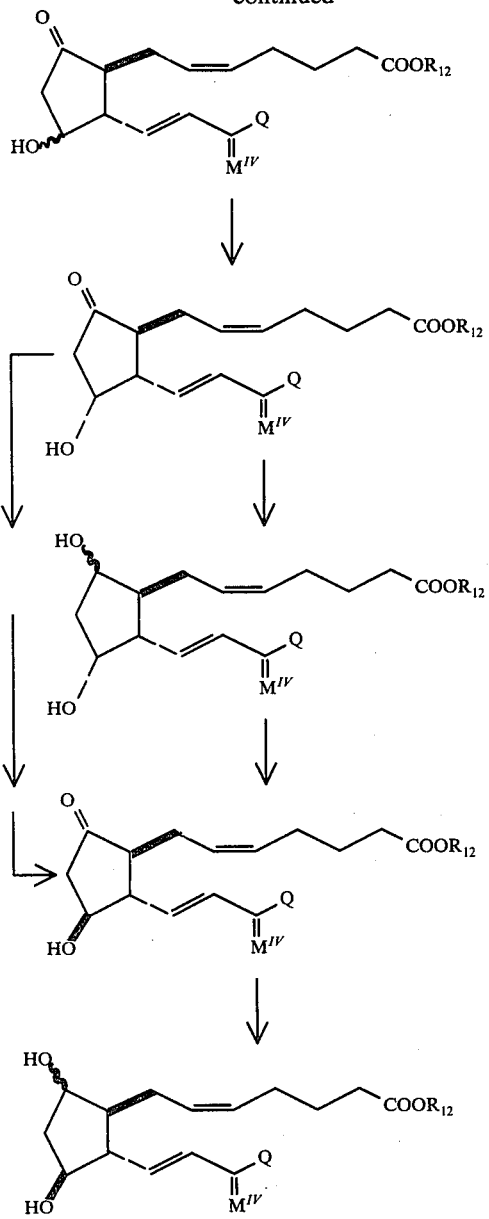

LXXVII

LXIV

LXV

LXXVIII

LXXIX presence of a Lewis acid, e.g. boron trifluoride etherate, aluminum chloride, or fluoboric acid. When $R_{22}$ is methyl, diazomethane is used. See Fieser et al., "Reagents for Organic Synthesis", John Wiley and Sons, Inc., N.Y. (1967), p. 191. Other —$OR_{22}$ groups are formed by using the corresponding diazoalkane. For example diazoethane and diazobutane yield —$OC_2H_5$ and —$OC_4H_9$ respectively. The reaction is carried out by mixing a solution of the diazoalkane in a suitable inert solvent, preferably ethyl ether, with the formula-XXVI compound. Generally the reaction proceeds at about 25° C. Diazoalkanes are known in the art or can be prepared by methods known in the art. See, for example, Organic Reactions, John Wiley and Sons, Inc. N.Y. Vol. 8, pp. 389-394 (1954).

Another method for the alkylation of the side chain hydroxy is by the reaction of an alcohol in the presence of boron trifluoride etherate. Thus, methanol and boron trifluoride etherate yield the methyl ether wherein $R_{22}$ is methyl. The reaction is done at about 25° C. and is conveniently followed with thin layer chromatography (TLC).

Another method for the alkylation of the side-chain hydroxy is by the reaction of an alkyl halide, e.g. methyl iodide, in the presence of a metal oxide or hydroxide, e.g. barium oxide, silver oxide, or barium hydroxide. An inert solvent may be beneficial, for example benzene or dimethylformamide. The reactants are preferably stirred together and maintained at temperatures of 25°–75° C.

Still another method is by first converting the hydroxy to mesyloxy (i.e. methanesulfonate) or tosyloxy (i.e. toluenesulfonate) and thence transforming the mexyloxy or tosyloxy to the —$OR_{22}$ moiety by reaction with a metal alkoxide, e.g. potassium tert-butoxide. The mesylate or tosylate is prepared by reaction of the formula-XXVI intermediate with either methanesulfonyl chloride or toluenesulfonyl chloride in pyridine. Thereafter, the mesylate or tosylate is mixed with the appropriate potassium or sodium alkoxide in pyridine, the reaction proceeding smoothly at about 25° C. An equivalent amount of the alkoxide based on the mesylate is preferred to avoid side reactions. In this manner, the formula-LVI intermediate is prepared wherein $R_{22}$ is normal alkyl, secondary alkyl, or tertiary alkyl of one to 5 carbon atoms. The method is especially useful for tertiary alkyl substitutions for hydrogen, e.g. where $R_2$ is tert-butyl or tert-pentyl.

The formula-LVII compound is then obtained by deacylation of LVI with an alkali metal carbonate, for example potassium carbonate in methanol at about 25° C.

The formula-LVIII compound is the same as the formula-LVII compound when $R_8$ is hydrogen, or is obtained from the formula-LVII compound by reactions discussed above when $R_8$ is a blocking group, such as tetrahydropyranyl, tetrahydrofuranyl, or silyl. Thereafter lactol LIX is obtained by reduction and converted to LX by a Wittig reaction. Thereafter the steps by which products LXI, LXIV, and LXV are obtained are analogous to those described above for Chart B.

Referring to Charts F and G, there are shown the steps by which the 11β analogs of the 15 alkyl ethers are prepared. The reactions are analogous to those shown above in Charts C and D. In Charts F and G, $M^{1\nu}$ is defined as it is in Chart E above. Starting material XL of Chart F is available by the processes of Chart C, discussed above. The formula-LXXIV 15-alkyl ether $PGA_2$ analogs of Chart F are useful per se and as intermediates for preparing the 11α 15-alkyl ether products LXIV and LXV according to Chart G.

As discussed above, the processes of Charts A-D, inclusive, lead variously to acids ($R_{12}$ is hydrogen) or to esters ($R_{12}$ is alkyl, cycloalkyl, aralkyl, phenyl or substituted phenyl, as defined above). When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for esterification of the carboxyl moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Examples of alkyl of one to 4 carbon atoms, inclusive, are methyl, ethyl, propyl, butyl, and isomeric forms thereof. Examples of phenylalkyl of 7 to 10 carbon atoms, inclusive, are benzyl, phenethyl, 1-phenylethyl, 2-phenylpropyl, 4-phenylbutyl, and 3-phenylbutyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3-methylphenyl. Examples of aralkyl of 7 to 12 carbon atoms, inclusive, other than the phenylalkyl examples above, are α-naphthylmethyl, and 2-(α-naphthyl)ethyl.

Examples of alkyl of one to 12 carbon atoms, inclusive, are, in addition to those alkyl examples above, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of alkyl of one to 18 carbon atoms, inclusive, are, in addition to those alkyl examples above, tridecyl, tetradecyl, pentadecyl, hexadecyl, heptadecyl, octadecyl, and isomeric forms thereof. Examples of phenyl substituted with one, 2, or 3 alkyl of one to 4 carbon atoms, inclusive, are (o, m, or p)-tolyl, 3,5-xylyl, (o, m, or p)-ethylphenyl, 2,5-diethylphenyl, (o, m, or p)-butylphenyl, (o, m, or p)-sec-butylphenyl, (o, m, or p)-tert-butylphenyl, 2-isopropyl-3-methylphenyl, (o, m, or p)-tert-butylhenyl, 2-isopropyl-3-methylphenyl, 2-ethyl-4-propylphenyl, 2,6-diisopropylphenyl, 3,4,5-trimethylphenyl, and 2,4,6-tributylphenyl.

When the processes of Charts A–D yield an ester, $R_{12}$ being methyl, the free acid products are obtained by methods known in the art. For example, the $PGF_2$ analogs are subjected to saponification in an aqueous alkaline medium to form an alkaline salt, which is then acidified to yield the free acid. A preferred method for the $PGE_2$ analogs, and useful for the $PGF_2$ analogs as well, is by enzymatic hydrolysis using an esterase enzyme composition obtained from the marine invertebrate Plexaura homomalla (Esper), 1792. Plexaura homomalla is a member of the subclass Octocorallia, order Gorgonacea, suborder Holaxonia, family Plexauridae, genus Plexaura. See, for example, Bayer, "The Shallow-Water Octocorallia of the West Indian Region", Martinus Nijhoff, The Hague (1961). Colonies of these Plexaura homomalla are abundant on the ocean reefs in the zone from the low-tide line to about 25 fathoms in the tropical and subtropical regions of the western part of the Atlantic Ocean, from Bermuda to the reefs of Brazil, including the eastern shore reefs of Florida, the Caribbean island and mainland reefs, and the Gulf of Mexico island and mainland reefs. These colonies are bush-like or small tree-like in habit and are readily identified for collection as Plexaura homomalla (Esper), 1792, by those of ordinary skill in this art. Two forms exist, the "R" form and the "S" form. See W. P. Schneider et al., J. Am. Chem. Soc. 94, 2122 (1972).

The esterase enzyme composition is produced by the steps: (1) extracting colonies or colony pieces of the marine invertebrate Plexaura homomalla (Esper), 1792, forma R or forma S, with liquid acetone for a sufficient time to remove substantially all soluble lipids, and (2) recovering the acetone-insoluble matter as said composition.

The colonies of Plexaura homomalla are used either in their as-harvested form or in broken or chopped pieces. It is immaterial whether they are used fresh from their natural environment, or after freezing and thawing, or even after drying under ambient conditions.

The extraction with acetone may be done batch-wise, as by stirring in a container, or by percolation, or by continuous methods of extraction known in the art. If stirring is used, it is advantageous to first chop the Plexaura homomalla into small pieces, for example less than 3 mm. in greatest dimension. The product is accordingly then a powder consisting of pieces smaller than 3 mm. Contact with acetone is continued until substantially all of the soluble lipids are removed. Normally one hour is sufficient, although a longer time is required for whole colonies and a shorter time is sufficient for chopped colonies with efficient extraction. The endpoint can be determined simply by examination of the acetone, as by evaporation and by physical measurements on any residue thus obtained. The extraction temperature is kept below 50° C. to avoid denaturation of the enzyme, and is preferably in the range 20° to 30° C. Lower temperatures may be used but the extraction then proceeds more slowly. The extraction is generally done at atmospheric pressure, but it may be carried out at higher or lower pressures provided the acetone is in a liquid state when contacting the Plexaura homomalla.

The acetone-insoluble enzyme composition is recovered from the acetone by decantation, filtration, centrifugation, or other convenient method for separating solids and liquids. A small amount of adherent acetone, for example, 10% of the weight of the composition, may be left on the product but it is preferred that the amount be lowered to less than 1%, for example by drying under ambient conditions or under reduced pressure. The product can then be stored without deterioration, preferably at about −20° C.

In utilizing the above esterase enzyme composition for the purposes of this invention, the prostaglandin ester is contacted with a mixture of the enzyme composition and water. The ester is conveniently added as a solution, for example in ethanol or benzene, to about 50–100 times its weight of water. The enzyme composition is added in an amount about 1–15 times the weight of ester. The mixture is stirred until the ester is hydrolyzed, generally about 18–24 hours at 25° C. Temperatures of about 0°–50° C. may be employed, although about 25° C. is preferred. The progress of hydrolysis is readily followed by analysis, for example by thin-layer chromatography by methods known in the art. See, for example, Hamberg et al., J. Biol. Chem. 241, 257 (1966). Finally, several volumes of acetone are added and the acid products dissolved in the acetone are recovered by filtration, concentration, and extraction using methods known in the art.

The final formula VI-to-XVII compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the formula VI-to-XVII acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula VI-to-XVII acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula VI-to-XVII acid with the stoichiometric amount of the corresponding quaternary ammonium hydroxide in water solution, followed by evaporation of the water.

The final formula VI-to-XVII acids or esters prepared by the processes of this invention are transformed to lower alkanoates by interaction of the formula VI-to-XVII hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography.

DESCRIPTION OF THE PREFERRED EMBODIMENTS

The invention can be more fully understood by the following preparations and examples.

All temperatures are in degrees centigrade.

Infrared absorption spectra are recorded on a Perkin-Elmer model 421 infrared spectrophotometer. Except when specified otherwise, undiluted (neat) samples are used.

Mass spectra are recorded on an Atlas CH-4 mass spectrometer with a TO-4 source (ionization voltage 70 ev).

NMR spectra are recorded on a Varian A-60 spectrophotometer in deuterochloroform solutions with tetramethylsilane as an internal standard (downfield).

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

"Skellysolve-B" refers to mixed isomeric hexanes.

Silica gel chromatography, as used herein, is understood to include elution, collection of fractions, and combination of those fractions shown by TLC (thin layer chromatography) to contain the desired product free of starting material and impurities.

Names of compounds used in these examples are understood to refer to compounds having the same configuration as the corresponding prostaglandins of natural configuration unless otherwise indicated in the name. For example, the product of Example 11, $8\beta,12\alpha$-PGE$_2$, methyl ester, has the alpha configuration at C-11 and at C-15, but has the 8-beta and 12-alpha configurations characteristic of the analogs of this invention.

Preparation 1

Dimethyl 2-Oxo-3-methylheptylphosphonate,

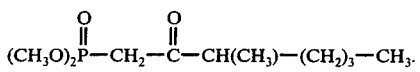

n-Butyllithium (150 ml.) is added slowly to a solution of dimethyl methylphosphonate (25.6 g.) in 475 ml. of tetrahydrofuran (THF) at about −65° C. To the mixture is added a solution of racemic ethyl 2-methylhexanoate (18.4 g.) in 50 ml. of THF, and the resulting mixture is stirred at −70° C. for 2 hrs. Then, 16 ml. of acetic acid is added, and the mixture is concentrated under reduced pressure. The residue is mixed with dichloromethane (about 400 ml.) and water (about 50 ml.), shaken, and separated. The organic phase is dried over magnesium sulfate and concentrated. Distillation yields the title compound, 16.7 g., b.p. 126°–129° C./1 mm.

Following the procedures of Preparation 1 but replacing racemic ethyl 2-methylhexanoate with the ethyl esters of the (+) and (−) isomers of 2-methylhexanoic acid (see P. A. Levene et al., J. Biol. Chem. 70, 211 (1926) and 84 571 (1929)) there are obtained the corresponding optically active (+) and (−) title compounds.

Preparation 2

Dimethyl 2-Oxo-3,3-dimethylheptylphosphonate,

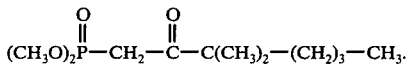

n-Butyllithium (400 ml.) is added slowly to a solution of dimethyl methylphosphonate (73.7 g.) in 1.3 l. of THF at about −66° C. To the mixture is added a solution of ethyl 2,2-dimethylhexanoate (53 g.) in 150 ml. of THF, and the resulting mixture is stirred at −70° C. for 2 hrs. Then, 46 ml. of acetic acid is added, and the mixture is concentrated under reduced pressure. The residue is mixed with portions of dichloromethane (about 1.2 l.) and water (about 150 ml.), shaken, and separated. The organic phase is dried over magnesium sulfate and concentrated. Distillation yields the title compound, 41.6 g., b.p. 117°–120° C./1 mm.

Preparation 3

Dimethyl 2-oxo-4-phenylbutylphosphonate,

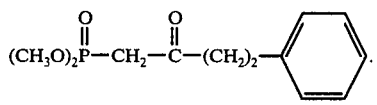

A solution of dimethyl methylphosphonate (115.5 g.) in 2.1 l. of tetrahydrofuran is treated, while stirring at −65° C., with a solution of butyl lithium (660 ml. 1.6 M. in hexane). A solution of ethyl hydrocinnamate (93.5 g.) in 225 ml. of tetrahydrofuran is added at −65° C. Stirring is continued at −65° C. for 2 hrs. and then at about 25° C. for 16 hrs. Acetic acid (70 ml.) is added and the mixture concentrated under reduced pressure. The residue is partitioned between dichloromethane and water. The organic phase is dried and concentrated. Distillation yields the title compound, b. 188°–191° C./2 mm., having a mass spectral peak at 256.

Preparation 4

Aluminum Amalgam.

Granular aluminum metal (50 g.) is added to a solution of mercuric chloride (50 g.) in 2 l. of water. The mixture is swirled until hydrogen gas evolution starts to become vigorous (about 30 seconds). Then, most of the aqueous solution is decanted, and the rest is removed by rapid filtration. The amalgamated aluminum is washed rapidly and successively with two 200-ml. portions of methanol and two 200-ml. portions of anhydrous diethyl ether. The amalgamated aluminum is then covered with anhydrous diethyl ether until used.

EXAMPLE 1

3β,5β-Dihydroxy-2α-methoxymethyl-1β-cyclopentaneacetic Acid γ-Lactone (Formula XX: $R_1$ is methyl).

A. Refer to Chart A. The formula-XIX iodo lactone is first prepared. For this purpose the formula-XVIII starting material of the proper configuration is obtained by resolution of the racemic hydroxy acid with (−)-ephedrine following the procedure of E. J. Corey et al. (J. Am. Chem. Soc. 92, 397 (1970)). The sodium salt of the laevorotatory formula-I hydroxy acid is then treated in water at 0°–5° C. with potassium triiodide (2.5 equivalents) for 20 hrs. to yield the formula-XIX compound, namely 3β,5β-dihydroxy-4-iodo-2α-methoxymethyl-1β-cyclopentaneacetic acid γ-lactone.

B. A solution of the product of step A (20.5 g.) in 125 ml. of benzene is treated at about 25° C. with 250 ml. of an ethereal solution (0.3 M.) of tributyltinhydride. When the reaction is complete, in approximately one hr. as shown by TLC (thin layer chromatography), the solution is concentrated under reduced pressure to a liquid residue. There is added 300 ml. of Skellysolve B (a mixture of isomeric hexanes) and 300 ml. of water, and the mixture is stirred for about 16 hrs. The aqueous phase, together with washings of the organic phase, is saturated with sodium chloride and extracted with ethyl acetate. The ethyl acetate solution is dried over sodium sulfate and concentrated to the title compound, an oil, 7.5 g; having infrared absorption at 3300, 1755, 1170, 1037, 959, and 890 cm$^{-1}$.

EXAMPLE 2

3β-p-Toluenesulfonyloxy-5β-hydroxy-2α-methoxymethyl-1β-cyclopentaneacetic Acid γ-Lactone (Formula XXI: $R_1$ is methyl and $R_2$ is p-toluenesulfonyl).

Refer to Chart A. A solution of the formula-XX compound (Example 1, 1.0 g.) in 20 ml. of pyridine is stirred at about 25° C. with p-toluenesulfonyl chloride (1.9 g.) for 2 days. The mixture is diluted with ice, made slightly acidic with 10% sulfuric acid, and extracted with ethyl acetate. The organic phase is washed with saturated sodium bicarbonate solution and brine, dried over sodium sulfate, and concentrated to the title compound, m.p. 85°–90° C., 1.8 g. An analytical sample has m.p. 97°–98° C., and NMR peaks at 7.80, 7.34, 5.1–4.7, 3.31, 3.23, and 2.98–2.12 δ.

EXAMPLE 3

3α-Benzoyloxy-5β-hydroxy-2α-methoxymethyl-1β-cyclopentaneacetic Acid γ-Lactone (Formula XXII: $R_1$ is methyl and $R_3$ is benzoyl)

Refer to Chart A. A mixture of the formula-XXI compound (1.8 g.) and sodium benzoate (5.0 g.) in 100 ml. of dimethyl sulfoxide is stirred at 80°–85° C. for 3.5 hrs. The mixture is then diluted with 500 ml. of ice water and extracted with diethyl ether. The organic phase is washed with saturated sodium bicarbonate solution and brine, dried over sodium sulfate, and concentrated to the title compound, an oil, 1.5 g; having NMR peaks at 8.30–7.91, 7.73–7.31, 5.80–5.55, 5.34–4.98, 3.74–3.43, 3.28, and 3.11–2.0 δ.

EXAMPLE 4

3α-Benzoyloxy-5β-hydroxy-2α-hydroxymethyl-1α-cyclopentaneacetic Acid γ-Lactone (Formula XXIII: $R_3$ is benzoyl)

Refer to Chart A. A solution of the formula-XXII compound (Example 3, 0.5 g.) in 20 ml. of ethyl acetate is treated at 0° C., while stirring, with 0.7 ml. of boron tribromide. After 0.5 hr., stirring is continued for 2 hrs. at about 25° C. There is then added 75 ml. of saturated sodium bicarbonate solution, the mixture is equilibrated, and the organic phase is washed with brine, dried over sodium sulfate, and concentrated to an oil, 0.47 g. The product is subjected to silica gel chromatography, eluting with 50% ethyl acetate in Skellysolve B, then 75% and finally ethyl acetate. Concentration under reduced pressure yields the title compound, an oil, 0.33 g; having infrared absorption at 3300, 1590, 1570, 1530, 1250, 1150, 1095, 1055, 1030, 1010, 900, 804, and 710 cm$^{-1}$; and NMR peaks at 8.17–7.83, 7.67–7.29, 5.76–5.57, 5.35–4.93, 3.27, and 3.13–1.95 δ.

EXAMPLE 5

3α-Benzoyloxy-5β-hydroxy-2α-(3-oxo-trans-1-octenyl)-1β-cyclopentaneacetic Acid γ-Lactone (Formula XXV: $R_3$ is benzoyl, $R_4$ and $R_5$ are hydrogen, and $R_6$ is n-butyl)

A. Refer to Chart A. There is first prepared the formula-XXIV aldehyde. A solution of the formula-XXIII compound (Example 4, 0.33 g.) in 2 ml. of dichloromethane is added to Collins reagent (prepared from 1.2 g. of pyridine and 1.0 g. of anhydrous chromium trioxide in 25 ml. of dichloromethane), with stirring at 0° C. After 5 min. at 0° C. and another 5 min. at about 25° C., the solution is decanted from the solids and used in step B below.

B. A solution of the appropriate ylide is prepared from a mixture of sodium hydride (0.12 g., 50%) and dimethyl 2-oxoheptylphosphonate (0.64 g.) in 22 ml. of tetrahydrofuran at 0° C. To the cold ylide solution is added the solution of the formula-XXIV aldehyde from step A and the mixture is stirred at about 25° C. for 4 hrs. The reaction mixture is added to a mixture of 150 ml. of 2 M. sodium hydrogen sulfate, and 100 ml. of diethyl ether. The organic phase is washed with saturated sodium bicarbonate solution and brine, dried over sodium sulfate, and concentrated to a dark liquid, 0.77 g. The residue is subjected to silica gel chromatography, eluting with 10% and 50% ethyl acetate in Skellysolve B. Concentration under reduced pressure yields the title compound, 0.28 g., as an oil which slowly crystallizes. An analytical sample, obtained by recrystallization from hexane-ethyl acetate, has m.p. 64°–65.5° C.; mass spectral peaks at 370, 248, and 192; optical rotation $[\alpha]_D$ $-149°$ (in chloroform); and NMR peaks at 8.13–7.82, 7.60–7.22, 7.10–6.64, 6.20, 5.75–5.50, 5.33–4.98, 4.29–3.91, and 3.45–0.57 δ.

EXAMPLE 6

3α-Benzoyloxy-5β-hydroxy-2α-(3α-hydroxy-trans-1-octenyl)-1β-cyclopentaneacetic Acid γ-Lactone (Formula XXVI: M is

Q is n-pentyl, and $R_3$ is benzoyl) and 3α-Benzoyloxy-5β-hydroxy-2α-(3β-hydroxy-trans-1-octenyl)-1β-cyclopentaneacetic Acid γ-Lactone (Formula XXVI: M is

and Q and $R_3$ are as defined above)

Refer to Chart A. A solution of the formula-XXV compound (Example 5, 0.61 g.) in 40 ml. of methanol is added to a mixture of sodium borohydride (90 mg.) in 40 ml. of methanol, with stirring at about $-15°$ C. under nitrogen. After 1.5 hrs., 5 ml. of acetic acid is added, the mixture left to warm to about 25° C., and then 5 ml. of water is added. Concentration under reduced pressure gives an oil which is dissolved in ethyl acetate and equilibrated with 0.2 M. sodium hydrogen sulfate. The organic phase, including washings of the aqueous phase, is washed with saturated sodium bicarbonate solution and brine, dried over sodium sulfate, and concentrated to an oil, 0.59 g. The residue is subjected to silica gel chromatography, eluting with 50% ethyl acetate-Skellysolve B, and dividing the eluant into 95 fractions. Fractions 48–56, when combined and concentrated, yield the 3β-hydroxy title compound, an oil, 0.16 g. Fractions 63–95 similarly yield the 3α-hydroxy title compound, an oil, 0.12 g.; having $R_f$ 0.35 (TLC on silica gel in 50% ethyl acetate-Skellysolve B) for the 3β-hydroxy compound, 0.30 for the 3α-hydroxy compound.

EXAMPLE 7

3α,5β-Dihydroxy-2α-(3α-hydroxy-trans-1-octenyl)-1β-cyclopentaneacetic Acid γ-Lactone (Formula XXVII: M is

and Q is n-pentyl)

Refer to Chart A. A mixture of the 3α-hydroxyoctenyl formula-XXVI compound (Example 6, 2.8 g.), potassium carbonate (1.4 g.), and 250 ml. of methanol is stirred for 24 hrs. at about 25° C. The solids are filtered off and the filtrate concentrated. The residue is taken up in ethyl acetate and equilibrated with brine. The organic phase is washed with brine, dried over sodium sulfate, and concentrated to the title compound, 1.9 g. as an oil which slowly crystallizes. An analytical sample, obtained by recrystallization from hexane-ethyl acetate, has m.p. 79°-81° C.; mass spectral peaks at 250, 193, and 179; and [α]$_D$ −39° (in chloroform).

Following the procedure of Example 7, but replacing the 3α-hydroxyoctenyl formula-XXVI compound of that example with the corresponding 3β-hydroxyoctenyl formula-XXVI compound (Example 6), there is obtained 3α,5β-dihydroxy-2α-(3β-hydroxy-trans-1-octenyl)-1β-cyclopentaneacetic acid γ-lactone, having R$_f$ 0.34 (TLC on silica gel in ethyl acetate).

EXAMPLE 8

3α,5β-Dihydroxy-2α-(3α-hydroxy-trans-1-octenyl)-1β-cyclopentaneacetic Acid γ-Lactone, Bis(tetrahydropyranyl) Ether (Formula-XXVIII: M is

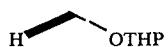

wherein THP is tetrahydropyranyl, Q is n-pentyl, and R$_8$ is tetrahydropyranyl).

Refer to Chart B. A solution of the 3α-hydroxyoctenyl formula-XXVII compound (Example 7, 1.7 g.) in dihydropyran (6.2 g.), pyridine hydrochloride (0.16 g.) and 37 ml. of dichloromethane is stirred at about 25° C. for 4 hrs. The solution is filtered through silica gel, and concentrated under reduced pressure to an oil, 2.8 g. The oil is subjected to silica gel chromatography, yielding the title compound, an oil, 1.7 g., having R$_f$ 0.63 (TLC on silica gel in 50% ethyl acetate Skellysolve B).

Following the procedure of Example 8, but replacing the 3α-hydroxyoctenyl formula-XXVII compound of that example with the 3β-hydroxyoctenyl formula-XXVII compound obtained following Example 7, there is obtained 3α,5β-dihydroxy-2α-(3β-hydroxy-trans-1-octenyl)-1β-cyclopentaneacetic acid γ-lactone, bis(tetrahydropyranyl) ether having R$_f$ 0.63 (TLC) on silica gel in 50% ethyl acetate-Skellysolve B).

EXAMPLE 9

3α,5β-Dihydroxy-2α-(3α-hydroxy-trans-1-octenyl)-1β-cyclopentaneacetaldehyde γ-Lactol, Bis(tetrahydropyranyl) Ether (Formula XXIX: M is

Q is n-pentyl, and R$_8$ is THP, wherein THP is tetrahydropyranyl, and ∼ is alpha or beta)

Refer to Chart B. A solution of the 3α-hydroxy-octenyl formula-XXVIII compound (Example 8, 1.7 g.) in 18 ml. of toluene is treated with stirring at −78° C. under nitrogen with 12.4 ml. of 10% diisobutylaluminum hydride in toluene. After one hr. there is added dropwise to the cold mixture 24 ml. of tetrahydrofuran-water (2:1) solution. The organic phase is filtered, washed with brine, dried over sodium sulfate, and concentrated to the title compound, an oil, 1.7 g. having R$_f$ 0.4 (TLC on silica gel in 50% ethyl acetate-Skellysolve B).

Following the procedure of Example 9, but replacing the 3α-hydroxyoctenyl formula-XXVIII compound of that example with the 3β-hydroxyoctenyl formula-XXVIII compound obtained following Example 8, there is obtained 3α,5β-dihydroxy-2α-(3β-hydroxy-trans-1-octenyl)-1β-cyclopentaneacetaldehyde γ-lactol, bis(tetrahydropyranyl) ether, having R$_f$ 0.4 (TLC on silica gel in 50% ethyl acetate-Skellysolve B).

EXAMPLE 10

8β,9β,12α-PGF$_2$, Methyl Ester, Bis(tetrahydropyranyl) Ether (Formula XXXII: M''' is

Q is n-pentyl, R$_8$ is THP (tetrahydropyranyl), and R$_{11}$ is methyl).

Refer to Chart B. There is first prepared the Wittig ylide. 4-Carboxybutyltriphenylphosphonium bromide (E. J. Corey et al., J. Am. Chem. Soc. 91, 5677 (1969)) (5.0 g.) is added to a solution of sodio dimethylsulfinyl-carbanide prepared from sodium hydride (50%, 1.1 g.) and 125 ml. of dimethylsulfoxide and the resulting solution is stirred 1.5 hrs. at about 25° C.

To the above solution is added a solution of the 3α-hydroxyoctenyl formula-XXIX compound (Example 9, 1.7 g.) in 50 ml. of dimethylsulfoxide and the resulting mixture is stirred at about 25° C. for 16 hrs. The mixture is then stirred with a mixture of aqueous 0.2 M. sodium hydrogen sulfate at pH about 3 and diethyl ether, and the two phases separated. The organic phase is extracted with aqueous 1 N. sodium hydroxide and then water, and the aqueous extract is acidified with aqueous 2 M. sodium hydrogen sulfate and extracted with diethyl ether. The organic extracts are washed with water and brine, dried over sodium sulfate, and concentrated to 8β,9β,12α-PGF$_2$ bis(tetrahydropyranyl) ether, an oil, 1.9 g. having R$_f$ 0.7 (TLC, silica gel plates, in A-IX solvent system).

The methyl ester is prepared by treating the above product in ether-methanol (1:1) solution at 0° C. with excess diazomethane, and concentrating the mixture to an oil, 1.8 g. Silica gel chromatography yields the title compound as an oil, 1.0 g., having R$_f$ 0.45 (TLC on silica fel in 50% ethyl acetate-Skellysolve B).

Following the procedure of Example 10, but replacing the 3α-hydroxyoctenyl formula-XXIX compound of that example with the 3β-hydroxyoctenyl formula-XXIX compound obtained following Example 9, there is obtained the corresponding C-15 epimer of the title compound, namely 8β,9β,12α,15β-PGF$_2$, methyl ester, bis(tetrahydropyranyl) ether, having R$_f$ 0.45 (TLC on silica gel in 50% ethyl acetate-Skellysolve B).

EXAMPLE 11

8β,12α-PGE$_2$, Methyl Ester (Formula XXXIV: M is

Q is n-pentyl, and R$_{12}$ is methyl)

Refer to Chart B. A solution of the 15α formula-XXX bis(tetrahydropyranyl) ether (Example 10, 1.0 g.) in 30 ml. of dichloromethane is added to previously cooled (0° C.) Collins reagent prepared from pyridine (2.6 g.) and chromium trioxide (1.7 g.) in 80 ml. of dichloromethane. The mixture is stirred at about 25° C. for 10 min. and filtered. The filtrate is concentrated to an oil. A solution of the oil in diethyl ether is washed with aqueous 0.2 M. sodium hydrogen sulfate, saturated aqueous sodium bicarbonate solution, and brine, dried over sodium sulfate, and concentrated to the bis(tetrahydropyranyl) ether of the title compound, an oil, 0.84 g., having $R_f$ 0.5 (TLC on silica gel in 50% ethyl acetate-Skellysolve B).

The above product is treated with 50 ml. of a solution of acetic acid, water, and tetrahydrofuran (20:10:3) at 40° C. for 3 hrs., cooled to 25° C., diluted with 70 ml. of water, and freeze-dried to the title compound, an oil, 0.74 g. Silica gel chromatography, taking 25 ml. fractions and eluting with 500 ml. of 20% acetone in dichloromethane, and 1000 ml. of 30% acetone in dichloromethane yields the title compound in fractions 21–26, an oil, 0.5 g., having mass spectral peaks (for the trimethylsilyl derivative) at 495, 492, 479, 420, and 349; and NMR peaks at 5.83–5.60, 5.50–5.20, 4.49–3.95, 3.67, and 2.98–0.67 δ.

There is also obtained, in fractions 8–10, 8β,12α-PGA$_2$ methyl ester, an oil, 0.06 g., having mass spectral peaks (for the trimethylsilyl derivative) at 420, 405, 389, 349, and 330.

Following the procedure of Example 11, but replacing the 15α formula-XXX compound of that example with the 15β formula-XXX compound obtained following Example 10, there is obtained 8β,12α,15β-PGE$_2$, methyl ester, having mass spectral peaks (for the trimethylsilyl derivative) at 510, 495, 492, 439, 420, and 349; NMR peaks at 5.82–5.69, 5.52–5.24, 4.49–4.00, 3.68 (singlet), and 2.75–0.73 δ; and $R_f$ 0.4 (TLC on silica gel in 30% acetone-dichloromethane).

There is also obtained, as a fraction in silica gel chromatography, 8β,12α,15β-PGA$_2$, methyl ester, having mass spectral peaks at 420, 405, 389, 349, and 330, and TLC $R_f$ 0.4 on silica gel in 10% acetone-dichloromethane.

EXAMPLE 12

8β,9α,12α-PGF$_2$, Methyl Ester (Formula XXXV: M is

Q is n-pentyl, R$_{12}$ is methyl, and ~ is alpha) and 8β,9β,12α-PGF$_2$, Methyl Ester (Formula XXXV: M is

Q is n-pentyl, R$_{12}$ is methyl, and ~ is beta).

Refer to Chart B. A solution of the 15α formula-XXXIV PGE$_2$ analog (Example 11, 0.2 g.) in 12 ml. of methanol is added, with stirring, to a slurry of sodium borohydride (0.03 g.) in 12 ml. of methanol at −15° C. under nitrogen and stirred for one hr. There is then added 10 ml. of acetic acid, dropwise, and the mixture is concentrated. The residue is triturated with ethyl acetate, separated, and the organic solution concentrated to an oil. Silica gel chromatography, eluting with 10% methanol in chloroform (saturated with boric acid) and collecting 10 ml. fractions, yields in fractions 8–11 the 9α title compound, about 0.11 g.; in fractions 12–15 the 9β title compound. Further processing of the 9α material by silica gel chromatography, eluting with 15–50% acetone in dichloromethane yields an analytical sample of the 9α title compound, an oil, 0.06 g., having mass spectral peaks (for the trimethylsilyl derivative) at 569, 553, 541, 513, 494, and 404; and NMR peaks at 5.84–5.37, 4.27–3.87, 3.67 (singlet), and 2.70–0.73 δ.

Following the procedure of Example 12, but replacing the 15α formula-XXXIV PGE$_2$ analog of that example with the 15β formula-XXXIV compound obtained following Example 11, there is obtained 8β,9α,12α,15β-PGF$_2$, methyl ester, having mass spectral peaks at 584, 569, 553, 541, 513, 494, and 404. Likewise there is obtained 8β,9β,12α-15β-PGF$_2$, methyl ester, having the same properties as the product following Example 13.

EXAMPLE 13

8β,9β,12α-PGF$_2$, Methyl Ester (Formula XXXI: M is

Q is n-pentyl, and R$_{12}$ is methyl)

Refer to Chart B. The 15α formula-XXX bis(tetrahydropyranyl) ether (Example 10, 0.46 g.) is treated with 28 ml. of a solution of acetic acid, water, and tetrahydrofuran (20:10:3) at 40° C. for 3 hrs., cooled, and freeze-dried to the title compound, an oil, 0.34 g. Silica gel chromatography, taking 20 ml. fractions and eluting with 250 ml. of 50% acetone in dichloromethane yields, from fractions 4–6, an analytical sample of the title compound, an oil, 0.21 g., having mass spectral peaks (for the trimethylsilyl derivative) at 569, 553, 541, 513, 494, and 404; and having NMR peaks at 5.75–5.30, 4.47–3.95, 3.67, and 2.70–0.73 δ.

Following the procedure of Example 13, but replacing the 15α formula-XXX compound of that example with the 15β formula-XXX compound obtained following Example 12, there is obtained 8β,9β,12α,15β-PGF$_2$, methyl ester, having mass spectral peaks at 584, 569, 553, 541, 513, 494, and 404; and NMR peaks at 5.75–5.30, 4.49–3.97, 3.68 (singlet), 2.53–0.72 δ.

EXAMPLE 14

3β-Benzoyloxy-5β-hydroxy-2α-methoxymethyl-1β-cyclopentaneacetic Acid γ-Lactone (Formula XXXVI: R$_1$ is methyl and R$_3$ is benzoyl)

A. Refer to Charts A and C. A solution of the formula-XIX iodo lactone (Example 1A, 18 g.) in 30 ml. of pyridine at 25° C. is mixed, while stirring, with 7.5 ml. of benzoyl chloride added dropwise and stirring is continued for one hr. The mixture is diluted with 60 ml. of toluene and concentrated to an oily residue. The residue is partitioned between ethyl acetate and 10% sulfuric acid. The organic phase is washed with saturated sodium bicarbonate and brine, dried over sodium sulfate, and concentrated to yield 3β-benzoyloxy-5β-hydroxy-4-iodo-2α-methoxymethyl-1β-cyclopentaneacetic acid γ-lactone, 21.8 g. An analytical sample has m.p. 85°–89° C., mass spectral peaks at 416, 294, 289, 262, 167, and 105, and optical rotation [α]$_D$ −5° C. in chloroform.

B. A solution of the product of part A (16.8 g.) in 100 ml. of benzene at 25° C. is mixed, with stirring, with 2.5 ml. of 0.3 M. tributyltin hydride in diethyl ether, and stirred for an additional 0.5 hr. The solution is concentrated to an oily residue. The residue is partitioned between 200 ml. of water and 200 ml. of Skellysolve B.

The aqueous phase is extracted first with Skellysolve B and then with ethyl acetate. The combined organic extracts are washed with brine, dried over sodium sulfate, and concentrated to the title compound, an oil, 11.2 g., having NMR peaks at 8.04–7.80, 7.54–7.14, 5.44–4.84, 3.35, 3.25, 3.03–1.95, and 1.38–0.86 δ.

EXAMPLE 15

3β-Benzoyloxy-5β-hydroxy-2α-hydroxymethyl-1β-cyclopentaneacetic Acid γ-Lactone (Formula XXXVII: R₃ is benzoyl)

Refer to Chart C. A solution of boron tribromide (175 g.) in 400 ml. of dichloromethane is added slowly to a stirred solution of the formula-XXXVI compound (Example 14, 101 g.) in 800 ml. of dichloromethane at 0° C. After 20 hrs. the reaction is quenched by careful addition of a solution of sodium carbonate (405 g. in 1050 ml. of water). The mixture is saturated with sodium chloride at about 25° C. and extracted with ethyl acetate. The organic phase is washed with brine, dried over sodium sulfate, and concentrated. The residue is recrystallized from dichloromethane-carbon tetrachloride, to yield the title compound, 85 g., m.p. 115°–116° C., having mass spectral peaks at 276, 154, and 136, optical rotation [α]$_D$ +81° in chloroform, and NMR peaks at 8.01–7.82, 7.54–7.14, 5.54–4.89, and 3.80–2.03 δ.

EXAMPLE 16

3β-Benzoyloxy-5β-hydroxy-2α-(3-oxo-trans-1-octenyl)-1β-cyclopentaneacetic Acid γ-Lactone (Formula XXXIX: Q is n-pentyl and R₃ is benzoyl)

A. Refer to Chart C. There is first prepared the formula-XXXVIII aldehyde. A solution of the formula-XXXVII compound (Example 15, 30.5 g.) in 300 ml. of dichloromethane is added to Collins reagent (prepared from 107 g. of pyridine and 84 g. of anhydrous chromium trioxide in 1500 ml. of dichloromethane), with stirring at 0° C. After 5 min. at 0° C. and another 5 min. at about 25° C., the solution is decanted from the solids and used in step B below.

B. The ylide is prepared from a mixture of sodium hydride (10.6 g., 50%) and dimethyl 2-oxoheptylphosphonate (48.8 g.) in 1600 ml. of tetrahydrofuran at 0° C. To the cold ylide solution is added the solution of the formula-XXXVIII aldehyde from step A and the mixture is stirred at about 25° C. for 4 hrs. The reaction mixture is added to a mixture of 2000 ml. of 2 M. sodium hydrogen sulfate and ice, then extracted with chloroform. The organic phase is washed with saturated sodium bicarbonate solution and brine, dried over sodium sulfate, and concentrated to an oily residue. The residue is taken up in diethyl ether and subjected to silica gel chromatography, eluting with 10% and 50% ethyl acetate in Skellysolve B. Concentration under reduced pressure yields the title compound, 26.2 g., as an oil which slowly crystallizes. An analytical sample, recrystallized from hexane-ethyl acetate, has m.p. 60°–62° C., and NMR peaks at 8.11–7.84, 7.62–7.20, 6.95–6.50, 6.17, 5.46–4.92, 3.52, and 3.10–0.62 δ.

EXAMPLE 17

3β-Benzoyloxy-5β-hydroxy-2α-(3α-hydroxy-trans-1-octenyl)-1β-cyclopentaneacetic Acid γ-Lactone (Formula XL: M is

Q is n-pentyl, and R₃ is benzoyl) and 3α-Benzoyloxy-5β-hydroxy-2α-(3β-hydroxy-trans-1-octenyl)-1β-cyclopentaneacetic Acid γ-Lactone (Formula XL: M is

and Q and R are as defined above)

Refer to Chart C. The formula-XXXIX compound (Example 16, 33.6 g.) in 250 ml. of methanol is added to a stirred mixture of sodium borohydride (5.30 g.) in 500 ml. of methanol at −20° C. under nitrogen. After 2 hrs., 250 ml. of acetic acid is added slowly at −20° C., and the solution is warmed to 25° C. and concentrated. The residue is partitioned between ethyl acetate and 0.2 M. sulfuric acid. The organic phase is washed with saturated aqueous sodium bicarbonate and brine, dried over sodium sulfate, and concentrated to a mixture of the title compounds, an oil, 41.6 g. Silica gel chromatography yields the separate title compounds; the 3α-hydroxy compound, m.p. 76.1°–76.9° C., having mass spectral peaks at 345, 301, and 250, and optical rotation [α]$_D$ +98° (chloroform); and the 3β-hydroxy compound, m.p. 69.0°–70.1° C., having mass spectral peaks at 314, 301, and 250, and optical rotation [α]$_D$ +77° (chloroform).

EXAMPLE 18

3β,5β-Dihydroxy-2α-(3α-hydroxy-trans-1-octenyl)-1β-cyclopentaneacetic Acid γ-Lactone (Formula XLI: M is

Q is n-pentyl, and R₈ is hydrogen)

Refer to Chart C. The formula-XL compound (Example 17, 10.2 g.) is stirred with potassium carbonate (5.62 g.) in 100 ml. of methanol at about 25° C. for 2 hrs. The mixture is filtered through silica gel and concentrated to an oil. The oil is partitioned between brine and ethyl acetate. The organic phase is dried over sodium sulfate and concentrated to a residual oil. The brine extract also yields an oil on acidification (2 M. sulfuric acid), extraction with ethyl acetate, and concentration. The combined oils are treated with pyridine hydrochloride (0.1 g.) in 250 ml. of ethyl acetate at reflux for one hour, filtered, and concentrated to the title compound, an oil, 6.9 g., having NMR peaks at 5.68–5.50, 5.13–4.76, 4.25–3.80, 3.70–3.08, and 2.97–0.67 δ.

Following the procedure of Example 18 but replacing the 3α-hydroxyoctenyl formula-XL compound of that example with the 3β-hydroxyoctenyl compound following Example 17, there is obtained the corresponding formula-XLI compound, namely 3β,5β-dihydroxy-2α-(3β-hydroxy-trans-1-octenyl)-1β-cyclopentaneacetic acid γ-lactone, having NMR peaks at 5.65–5.43, 5.07–4.74, 4.25–3.76, 3.54–3.28, and 2.92–0.50 δ.

EXAMPLE 19

3β,5β-Dihydroxy-2α-(3α-hydroxy-trans-1-octenyl)-1β-cyclopentaneacetic Acid γ-Lactone, bis(tetrahydropyranyl) Ether (Formula XLI: M' is

Q is n-pentyl, and $R_8$ is THP)

Refer to Chart C. A solution of the formula-XLI compound (Example 18, 0.66 g.) in 20 ml. of dichloromethane, together with dihydropyran (2.5 g.) and pyridine (0.075 g.) is stirred at about 25° C. for 24 hrs. The mixture is filtered through silica gel and concentrated to an oil, 1.2 g. Silica gel chromatography yields the title compound, an oil, 0.67 g., having $R_f$ 0.5 (TLC on silica gel in 50% ethyl acetate-Skellysolve B).

Following the procedure of Example 19 but replacing the 3α-hydroxyoctenyl formula-XLI compound with the corresponding 3β-hydroxyoctenyl compound following Example 18, there is obtained 3β,5β-dihydroxy-2α-(3β-hydroxy-trans-1-octenyl)-1β-cyclopentaneacetic acid γ-lactone, bis(tetrahydropyranyl) ether, having $R_f$ 0.5 (TLC on silica gel in 50% ethyl acetate-Skellysolve B).

EXAMPLE 20

3β,5β-Dihydroxy-2α-(3α-hydroxy-trans-1-octenyl)-1β-cyclopentaneacetic Acid γ-Lactol, Bis(tetrahydropyranyl), Ether (Formula XLII: M' is

Q is n-pentyl, and $R_8$ is THP)

Refer to Chart C. A solution of the formula-XLI compound (Example 19, 0.67 g.) in 20 ml. of toluene is treated, while stirring at −78° C. under nitrogen, with 5 ml. of 10% diisobutylaluminum hydride in toluene. After one hr. there is slowly added to the cold mixture 24 ml. of tetrahydrofuran-water (2:1) solution. The organic phase is filtered, washed with brine, dried over sodium sulfate, and concentrated to the title compound, an oil, 0.67 g., having TLC $R_f$ 0.3 on silica gel in 50% ethyl acetate-Skellysolve B.

Following the procedure of Example 20 but replacing the 3α-hydroxyoctenyl formula-XLI compound of that example with the corresponding 3β-hydroxyoctenyl compound following Example 19 there is obtained 3β,5β-dihydroxy-2α-(3β-hydroxy-trans-1-octenyl)-1β-cyclopentaneacetic acid γ-lactol, bis(terehydroyranyl) ether, an oil, having $R_f$ 0.3 (TLC on silica gel in 50% ethyl acetate-Skellysolve B).

EXAMPLE 21

8β,9β,11β,2α-PGF$_2$, Methyl Ester, Bis(tetrahydropyranyl) Ether (Formula XLIII: M' is

Q is n-pentyl, $R_{10}$ is THP, and $R_{12}$ is methyl)

Refer to Chart C. Following the procedure of Example 10, the Wittig ylide prepared from 4-carboxybutyl-triphenylphosphonium bromide is eacted with the 3α-hydroxyoctenyl formula-XLII compound (Example 20, 10.7 g.). Thereafter, following the procedure of Example 10, the title compound is obtained, an oil, 0.55 g., having $R_f$ 0.6 (TLC on silica gel in 50% ethyl acetate-Skellysolve B).

Likewise following the procedure of Example 10, but employing the 3β-hydroxyoctenyl formula-XLII compound following Example 20 (18.2 g.), there is obtained the corresponding C-15 epimer of the title compound, namely 8β,9β,11β,12α,15β-PGF$_2$, methyl ester, bis(tetrahydropyranyl) ether, an oil, 12.5 g., having $R_f$ 0.5 (TLC on silica gel in 50% ethyl acetate-Skellysolve B).

EXAMPLE 22

8β,11β,12α-PGE$_2$, Methyl Ester (Formula XLVI: M'''is

Q is n-pentyl, $R_8$ is hydrogen, and $R_{12}$ is methyl)

Refer to Chart C. Following the procedures of Example 11, the 15α formula-XLIII PGF$_2$-type compound (Example 21, 0.55 g.) is treated with Collins reagent to yield the corresponding bis(tetrahydroyranyl) ether of the title compound, an oil, 0.50 g., having $R_f$ 0.6 (TLC on silica gel in 50% ethyl acetate-Skellysolve B).

Following the procedures of Example 11, the above product is treated with acetic acid-water-tetrahydrofuran to yield the title compound, an oil, 0.17 g. having mass spectral peaks at 495, 479, 439, 420, and 349; NMR peaks at 5.77–5.60, 5.50–5.26, 4.32–3.87, 3.67 (singlet), and 3.05–0.61 δ; and optical rotation $[\alpha]_D$ +67° (in tetrahydrofuran).

As in Example 11, there is also obtained the PGA$_2$ analog, namely 8β,12α,15α-PGA$_2$ methyl ester.

Likewise following the procedures of Example 11, but employing the 15β formula-XLIII PGF$_2$-type compound (Example 21, 12.5 g.) there are obtained the corresponding C-15 epimers of the above compounds, namely: 8β,11β,12α,15β-PGE$_2$, methyl ester, bis(tetrahydropyranyl) ether, having $R_f$ 0.6 (TLC on silica gel in 50% ethyl acetate-Skellysolve B). 8β,11β,12α,15β-PGE$_2$, methyl ester, having mass spectral peaks at 495, 492, 439, 420, and 349, NMR peaks at 5.72–5.37, 4.32–3.83, 3.68 (singlet), and 2.75–0.69 δ, and optical rotation $[\alpha]_D$ +55° (in tetrahydrofuran); and 8β,12α,15β-PGA$_2$, methyl ester.

EXAMPLE 23

8β,9α,11β,12α-PGF$_2$, Methyl Ester (Formula LIV: M is

Q is n-pentyl, R$_{12}$ is methyl, and ~ is alpha) and 8β,9β,11β,12α-PGF$_2$, Methyl Ester (Formula LIV: M is

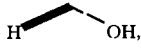

Q is n-pentyl, R$_{12}$ is methyl, and ~ is beta).

Refer to Chart D. Following the procedures of Example 12, the 15α formula-LIII 8β,11β,12α-PGE$_2$, methyl ester (Example 22, 0.12 g.) is reduced with sodium borohydride, yielding the title compounds. The 9α title compound is the more polar material, an oil, 0.021 g., having mass spectral peaks at 569, 553, 541, 513, and 494. The 9β title compound is an oil, having mass spectral peaks at 569, 553, 541, 513, and 494; NMR peaks at 6.10–5.32, 4.32–3.81, 3.67 (singlet), and 2.60–0.76 δ; and optical rotation [α]$_D$ −9° (in tetrahydrofuran).

Likewise following the procedures of Example 12, but employing the 15β formula-LIII compound, namely 8β,11β,12α,-15β-PGE$_2$, methyl ester (Example 22, 1.0 g.) the corresponding C-15 epimers of the above compounds are obtained, namely: 8β,9α,11β,12α,15β-PGF$_2$, methyl ester, m.p. 90°–91° C., having mass spectral peaks at 569, 553, 541, 503, 494, 479, 463, and 457; NMR peaks at 5.64–5.34, 4.17–3.78, 3.67 (singlet), and 3.00–0.45 δ; and optical rotation [α]$_D$ +7° (in ethanol); and 8β,9β,11β,12α,15β-PGF$_2$, methyl ester, identical with the 15β product of Example 24.

EXAMPLE 24

8β,9β,11β,12α-PGF$_2$, Methyl Ester (Formula LIV: M is

Q is n-pentyl, R$_{12}$ is methyl, and ~ is beta).

Following the procedure of Example 12, the 15α formula-XLIII 8β,9β,11β,12α-PGF$_2$, methyl ester, bis(-tetrahydropyranyl) ether (Example 21, 0.11 g.) is treated in acetic acid-water-tetrahydrofuran to yield the title compound having the same properties as the 15α product of Example 23.

Likewise following the procedure of Example 13, but employing the 15β formula-XLIII compound, namely 8β,9β,11β,12α,15β-PGF$_2$, methyl ester, bis(tetrahydropyranyl) ether following Example 21, there is obtained the corresponding C-15 epimer of the title compound, namely 8β,9β,11β,12α,15β-PGF$_2$, methyl ester, an oil, having mass spectral peaks at 569, 553, 541, 513, 423, and 404. NMR peaks at 5.64–5.26, 4.27–3.77, 3.67 (singlet), 3.34–2.86, and 2.53–0.67 δ; and optical rotation [α]$_D$ −24° (in ethanol).

EXAMPLE 25

3β-Benzoyloxy-5β-hydroxy-2α-(3-methyl-trans-1-octenyl)-1β-cyclopentaneacetic Acid γ-Lactone (Formula XL: M is

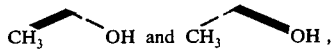

Q is n-pentyl, and R$_3$ is benzoyl).

Refer to Chart C. A solution of the formula-XXXIX compound (Example 16, 0.20 g.) in 15 ml. of tetrahydrofuran is treated, while stirring at −78° C., with methyl magnesium bromide (3 M. solution in diethyl ether) added dropwise. After 2 hrs. stirring, 10 ml. of saturated aqueous ammonium chloride is added dropwise and the mixture is warmed to 25° C. The mixture is diluted with diethyl ether and water, equilibrated, and separated. The organic phase is washed with brine, dried over sodium sulfate, and concentrated to the title compounds, on oil.

EXAMPLE 26

3β,5β-Dihydroxy-2α-(3-methyl-trans-1-octenyl)-1β-cyclopentaneacetic Acid γ-Lactone (Formula XLI: M' is

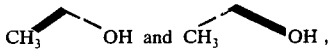

Q is n-pentyl, and R$_8$ is hydrogen).

Refer to Chart C. A solution of the formula-XL compounds (Example 25, 0.50 g.) in 10 ml. of methanol is treated, while stirring at about 25° C. under nitrogen, with 1.0 ml. of a 25% solution of sodium methoxide in methanol. After 20 min., 2 ml. of acetic acid is added, and the mixture is concentrated under reduced pressure to an oil. The residue is dissolved in ethyl acetate and extracted with saturated aqueous sodium bicarbonate. The organic phase is washed with brine, dried over sodium sulfate, and concentrated to the title compounds, a yellow oil.

EXAMPLE 27

3β,5β-Dihydroxy-2α-(3-methyl-trans-1-octenyl)-1β-cyclopentaneacetic Acid γ-Lactol (Formula XLII: M' is

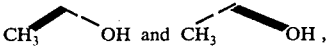

Q is n-pentyl, and R$_8$ is hydrogen).

Refer to Chart C. A solution of the formula-XLI compounds (Example 26, 0.50 g.) in 15 ml. of tetrahydrofuran is treated, while stirring at −78° C. under nitrogen, with 12 ml. of 12% diisobutylaluminum hydride in toluene. Saturated aqueous ammonium chloride (15 ml.) is added. The reaction mixture is warmed to 25° C., shaken with ethyl acetate and water, and filtered. The filtrate is equilibrated with brine and ethyl acetate. The organic phase is washed with brine, dried over sodium sulfate, and concentrated to the title compounds, an oil.

EXAMPLE 28

Mixed 15-Epimers of 15-Methyl-8β,9β,11β,12α-PGF$_2$, Methyl Ester (Formula XLIII: M''' is

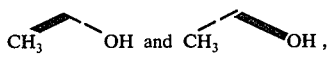

Q is n-pentyl, R$_{10}$ is hydrogen, and R$_{12}$ is methyl).

Refer to Chart C. The formula-XLII compounds (Example 27, 0.51 g. are added to a Wittig reagent prepared from 4-carboxybutyl triphenylphosphonium bromide (2.4 g.) and sodio dimethylsulfinylcarbanide (from 0.52 g. of 50% sodium hydride and 15 ml. of dimethylsulfoxide). The reaction mixture is stirred at about 25° C. for 16 hrs., and then added to a mixture of 0.2 M. sodium bisulfate in ice water and diethyl ether, whereby the resulting pH is about 1.0. After equilibration, the aqueous phase is extracted with diethyl ether. The organic extracts are combined, washed with 1 N. sodium hydroxide and water. The aqueous washings are combined and acidified to pH less than 3.0 with 2 M. sodium bisulfate. The mixture is extracted with diethyl ether, and the organic phase is washed with water, dried over sodium sulfate, and concentrated to the free acids corresponding to the title compounds (wherein R$_{12}$ is hydrogen), an oil.

The above product is dissolved in ether, dichloromethane, and methanol, and treated with excess ethereal diazomethane to give the title compounds, an oil.

EXAMPLE 29

15-Methyl-8β,9β,11β,12α-PGF$_2$, Methyl Ester (Formula-XLIV: M''' is

Q is n-pentyl, R$_9$ is hydrogen, and R$_{11}$ is methyl) and its C-15 epimer, 15-Methyl-8β,9β,11β,12α,15β-PGF$_2$, Methyl Ester The formula-XLIII mixed C-15 epimers of Example 28 are subjected to silica gel chromatography, eluting with 30% acetone in dichloromethane. The less polar compound is the 15α isomer, obtained by combining the early (less polar) fractions. The 15β title compound is obtained by combining the later fractions.

The 15α isomer has mass spectral peaks at 583, 527, 508, 437, and 418; NMR peaks at 5.7–5.2, 4.35–3.80, 3.70 (singlet), 1.28 (singlet), and 2.6–0.7 δ; optical rotation [α]$_D$ −29° (in ethanol).

The 15β isomer has mass spectral peaks at 583, 528, 508, 437, and 418; NMR peaks at 5.7–5.2, 4.35–3.80, 3.70 (singlet), 1.28 (singlet), and 2.6–0.7 δ; optical rotation [α]$_D$ −25° (in ethanol).

EXAMPLE 30

15-Methyl-8β,11β,12α-PGE$_2$, Methyl Ester (Formula-XLVI: M''' is

Q is n-pentyl, R$_9$ is hydrogen, and R$_{11}$ is methyl).

A. Refer to Chart C. The formula-XLIV 15-methyl-8β,9β,11β,12α-PGF$_2$, methyl ester, 11-trimethylsilyl ether is first prepared. A solution of the formula-XLIV 15-methyl-8β,9β,11β,12α-PGF$_2$, methyl ester (Example 29, 0.50 g.) in 20 ml. of acetone is treated, while stirring at −45° C. under nitrogen, dropwise with 2.0 ml. of N-trimethylsilyldiethylamine. After one hour at −45° C., the solution is diluted with 80 ml. of diethyl ether and partitioned with 5% aqueous sodium bicarbonate. The organic phase is washed with brine, dried over sodium sulfate, and concentrated to the 11-trimethylsilyl ether.

B. The product of step A (0.61 g.) in 15 ml. of dichloromethane is added to Collins reagent at 0° C. (previously prepared from 1.0 g. of chromium trioxide, 1.6 g. pyridine, and 50 ml. of dichloromethane). The mixture is stirred for 10 min., then decanted and filtered. The filtrate is concentrated under reduced pressure to the formula-XLV 15-methyl-8β,11β,12α-PGE$_2$, methyl ester, 11-trimethylsilyl ether.

C. The product of step B (0.57 g.) in 30 ml. of methanol is treated, while stirring at about 25° C., with a solution of 1.5 ml. of acetic acid in 15 ml. of water. After the mixture is homogeneous, it is partitioned between diethyl ether and 0.2 M. sodium hydrogen sulfate. The organic phase is washed with saturated aqueous sodium bicarbonate and brine, dried over sodium sulfate, and concentrated. The residue is subjected to silica gel chromatography to obtained the title compound, having mass spectral peaks at 519, 493, 453, 434, 363, and 344; NMR peaks at 5.7–5.2, 4.4–3.8, 3.68 (singlet), 1.28 (singlet) and 3.0–0.7 δ; and optical rotation [α]$_D$ +78° (in chloroform).

Following the procedures of Example 30, but replacing the formula-XLIV 15-methyl-8β,9β,11β,12α-PGF$_2$, methyl ester with the formula-XLIV 15-methyl-8β,9β,11β,12α,15β-PGF$_2$, methyl ester (Example 29), there are obtained, respectively:

15-methyl-8β,9β,11β,12α,15β-PGF$_2$, methyl ester, 11-trimethylsilyl ether, 15-methyl-8β,11β,12α,15β-PGE$_2$, methyl ester, 11-trimethylsilyl ether, and 15-methyl-8β,11β,12α,15β-PGE$_2$, methyl ester.

The last-named compound has a mass spectral peak at 524.3326 for the silylated derivative; NMR peaks at 5.7–5.2, 4.4–3.8, 3.67 (singlet), 1.29 (singlet), and 3.0–0.7 δ; and optical rotation [α]$_D$ +77° (in chloroform).

EXAMPLE 31

15-Methyl-8β,9α,11β,12α-PGF$_2$, Methyl Ester (Formula-LIV: M is

Q is n-pentyl, R$_{12}$ is methyl, and ∼ is alpha).

Refer to Chart D. The formula-LIII 15-methyl-8β,11β,12α-PGE$_2$, methyl ester (Example 30, 0.12 g.) is added to a stirred mixture of sodium borohydride (0.018 g.) in 6 ml. of methanol at −20° C. under nitrogen. After 30 min., 6 ml. of acetic acid is added, the mixture is warmed to about 25° C., and concentrated. The residue is dissolved in ethyl acetate and washed with 0.2 M. sulfuric acid. The organic phase is washed with saturated aqueous sodium bicarbonate and brine, dried over sodium sulfate, and concentrated. The mixed C-9 epimers are separated by silica gel chromatography, the less polar material being 15-methyl-8β,9β,11β,12α-PGF₂, methyl ester; the more polar material being the title compound (43% yield) having R_f 0.13 (TLC on silica gel in 30% acetone in dichloromethane) and mass spectral peaks (for the trimethylsilyl derivative) at 583, 567, 527, 508, 493, 486, and 217.

Following the procedures of Example 31 but replacing the formula-LIII 15-methyl-8β,11β,12α-PGE₂, methyl ester with the formula-LIII 15-methyl-8β,11β,12α,15β-PGE₂, methyl ester following Example 30, there are obtained 15-methyl-8β,9β,11β,12α,15β-PGF₂, methyl ester, and 15-methyl-8β,9α,11β,12α,15β-PGF₂, methyl ester.

EXAMPLE 32

15-Methyl-8β,12α-PGA₂, Methyl Ester (Formula XLVII: M' is

Q is n-pentyl, and R₁₂ is methyl).

A. Refer to Chart C. There is first prepared 15-methyl-8β,11β,12α-PGE₂, 11-acetate, methyl ester. A solution of the formula-XLVI 15-methyl-8β,11β,12α-PGE₂, methyl ester (Example 30, 0.52 g.) in 52 ml. of pyridine is treated, while stirring at about 25° C. under nitrogen, with 5.4 ml. of acetic anhydride. After 5 hrs. stirring, the mixture is added to 500 ml. of 2 M. sodium hydrogen sulfate, ice, and ethyl acetate, and equilibrated. The organic phase is washed with saturated aqueous sodium bicarbonate and brine, dried over sodium sulfate, and concentrated to an oil, 0.68 g., having R_f 0.34 (TLC on silica gel in 5% acetone-dichloromethane).

B. The 11-acetate from step A (0.68 g.) is stirred with potassium acetate (1.2 g.) in 45 ml. of methanol at about 25° C. After 18 hrs. the mixture is added to a mixture of saturated aqueous sodium bicarbonate and ethyl acetate, and equilibrated. The organic phase is washed with brine, dried over sodium sulfate, and concentrated to the title compound, an oil, 0.51 g., having R_f 0.41 (TLC on silica gel in 5% acetone-dichloromethane); and NMR peaks at 7.6–7.4, 6.25–6.05, 5.6–5.3, 3.67 (singlet), 3.4–3.1, 1.27 (singlet), and 2.7–0.7 δ.

EXAMPLE 33

15-Methyl-8β,12α-PGA₂, 10,11-Epoxide, Methyl Ester (Formula XLVIII: M''' is

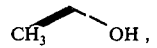

Q is n-pentyl, and R₂₀ is methyl).

Refer to Chart D. The formula-XLVII compound (Example 32, 0.18 g.) in 5 ml. of methanol is treated, while stirring at −25° C. under nitrogen, with a solution of 0.7 ml. of 30% aqueous hydrogen peroxide and 0.35 ml. of 1 N. sodium hydroxide. After one hour, there is added 2 N, hydrochloric acid dropwise to pH 5–6. The mixture is diluted with brine and extracted with diethyl ether. The organic phase is washed with saturated aqueous sodium bicarbonate and brine, dried over sodium sulfate, and concentrated to the title compound, an oil.

EXAMPLE 34

15-Methyl-8β,12α-PGE₂, Methyl Ester (Formula L: M is

Q is n-pentyl, and R₁₂ is methyl) and 15-Methyl-8β,11β,12α-PGE₂, Methyl Ester (Formula L: M is

Q is n-pentyl, ~ is beta, and R₁₂ is methyl).

Refer to Chart D. A mixture of the formula-XLVIII 15-methyl-8β,12α-PGA₂, 10,11-epoxide, methyl ester (Example 33, 0.20 g.), aluminum amalgam (Preparation 4, 0.16 g.), 8 ml. of diethyl ether, 1.6 ml. of methanol, and 4 drops of water is stirred at about 25° C. for 48 hrs. The mixture is filtered and the filtrate is concentrated to the mixed title compounds, an oil, 0.17 g. Separation by silica gel chromatography eluting with ethyl acetate-Skellysolve B yields the 11α compound as the less polar compound, and the 11β compound as the more polar compound. The 11α isomer has NMR peaks at 5.8–5.6, 5.5–5.2, 4.5–4.2, 3.67 (singlet), 1.30 (singlet), 3.0–0.7 δ.

EXAMPLE 35

15-Methyl-8β,12α,15β-PGE₂, Methyl Ester (Formula LI: M is

Q is n-pentyl, and R₁₂ is methyl) and 15-Methyl-8β,11β,12α,15β-PGE₂, Methyl Ester) Formula LIII: M is

Q is n-pentyl, and R₁₂ is methyl).

Refer to Charts C and D. Following the procedures of Example 32 but replacing the formula-XLVI 15-methyl-8β,11β,12α-PGE₂, methyl ester of that example with the formula-XLVI 15-methyl-8β,11β,12α,15β-PGE₂, methyl ester following Example 30, there are obtained, respectively 15-methyl-8β,11β,12α,15β-PGE₂, 11-acetate, methyl ester and 15-methyl-8β,12α,15β-PGA₂, methyl ester.

Following the procedure of Example 33 but employing the above PGA₂ analog, there is obtained the formula-XLVIII 15-methyl-8β,12α,15β-PGA₂, 10,11-epoxide, methyl ester.

Finally, following the procedure of Example 34, the above PGA₂ epoxide analog is transformed to the title compounds. The formula-LI (11α) compound (obtained in 23% yield) has $R_f$ 0.5 (TLC on silica gel in 30% acetone in dichloromethane; mass spectral peaks (for the trimethylsilyl derivative) at 537, 535, 493, 453, 434, 419, 363, 344, and 309; and NMR peaks at 5.84–5.60, 5.48–5.24, 4.50–4.24, 4.50–4.25, 3.68 (singlet) and 3.20–0.67 δ.

EXAMPLE 36

15-Methyl-8β,9α,12α-PGF$_2$, Methyl Ester (Formula LII: M is

Q is n-pentyl, and $R_{12}$ is methyl) and 15-Methyl-8β,9β,12α-PGF$_2$, Methyl ester (Formula LII: M is

Q is n-pentyl, and $R_{12}$ is methyl).

Refer to Chart D. Following the procedures of Example 12, but replacing the 15α formula-XXXIV PGE$_2$ analog of that example with the formula-LI 15-methyl-8β,12α-PGE$_2$, methyl ester of Example 34, yields after silica gel chromatography the title compounds. The 9α compound (obtained in 39% yield) has $R_f$ 0.3 (TLC on boric acid-impregnated silica gel in chloroform-methanol-acetic acid (95-5-1)); mass spectral peaks (for the trimethylsilyl derivative) at 508, 455, 418, and 217; and NMR peaks at 5.82–5.35, 4.26–3.77, 3.68 (singlet), and 3.17–0.68. The 9β compound (obtained in 4% yield) has $R_f$ 0.1 (TLC on boric acid-impregnated silica gel in chloroform-methanol-acetic acid (95-5-1)) and mass spectral peaks at 583, 567, 527, and 508.

Likewise following the procedures of Example 12 but employing the formula-LI 15-methyl-8β,12α,15β-PGE$_2$, methyl ester of Example 35, there are obtained 15-methyl-8β,9α,12α,15β-PGF$_2$, methyl ester, and 15-methyl-8β,9β,12α,15β-PGF$_2$, methyl ester. The 9α compound (obtained in 68% yield) has $R_f$ 0.3 (TLC on boric acid-impregnated silica gel in chloroform-methanol-acetic acid (95-5-1); mass spectral peaks (for the trimethylsilyl derivative) at 583, 527, 508, 455, and 418; infrared absorption at 3400, 2950, 1740, 1413, 1210, 1083, 976, and 758 cm$^{-1}$; and NMR peaks at 5.80–5.10, 4.14–3.80, 3.68 (singlet), 3.16 (singlet), and 2.57–0.62 δ.

EXAMPLE 37

16-Methyl-8β,12α-PGE$_2$, Methyl Ester (Formula XXXIV: M is

Q is —CH(CH$_3$)—(CH$_2$)$_3$—CH$_3$, and $R_{12}$ is methyl).

Refer to Charts A and B. Following the procedures of Examples 5 and 6, but replacing the ylide of Example 5 with the ylide prepared from dimethyl 2-oxo-3-methylheptylphosphonate (Preparation 1), there are obtained the corresponding formula-XXV compounds, 3α-benzoyloxy-5β-hydroxy-2α-(3α-hydroxy-4-methyl-trans-1-octenyl)-1β-cyclopentaneacetic acid γ-lactone and 3α-benzoyloxy-5β-hydroxy-2α-(3β-hydroxy-4-methyl-trans-1-octenyl)-1β-cyclopentaneacetic acid γ-lactone.

Thereafter, following the procedures of Examples 7-11, inclusive, the above 3α-hydroxy-4-methyloctenyl intermediates are transformed to the above title compounds.

Likewise following the procedures of Example 7-11, inclusive, but employing the 3β-hydroxy-4-methyloctenyl intermediates above, there are obtained the corresponding C-15 epimers, namely 16-methyl-8β,12α,15β-PGE$_2$, methyl ester.

EXAMPLE 38

16-Methyl-8β,9α,12α-PGF$_2$, Methyl Ester (Formula XXXV: M is

Q is —CH(CH$_3$)—(CH$_2$)$_3$—CH$_3$, and $R_{12}$ is methyl) and 16-Methyl-8β,9β,12α-PGF$_2$, Methyl Ester (Formula XXXV: M is

Q is —CH(CH$_3$)—(CH$_2$)$_3$—CH$_3$, and $R_{12}$ is methyl).

Refer to Chart B. Following the procedures of Example 12, but replacing the 15α formula-XXXIV PGE$_2$ analog of that example with the product of Example 37, namely 16-methyl-8β,12α-PGE$_2$, methyl ester, the above title compounds are obtained.

Likewise following the procedures of Example 12, but employing the 15β analog, namely 16-methyl-8β,12α,15β-PGE$_2$, methyl ester obtained following Example 37, there are obtained the corresponding C-15 epimers, namely 16-methyl-8β,9α,12α,15β-PGF$_2$, methyl ester, and 16-methyl-8β,9β,12α,15β-PGF$_2$, methyl ester.

EXAMPLE 39

16-Methyl-8β,11β,12α-PGE$_2$, Methyl Ester (Formula XLVI: M''' is

Q is —CH(CH$_3$)—(CH$_2$)$_3$—CH$_3$, $R_8$ is hydrogen, and $R_{12}$ is methyl).

Refer to Charts A and C. Following the procedures of Example 16 and 17, but replacing the ylide of Example 16 with the ylide prepared from dimethyl 2-oxo-3-methylheptylphosphonate (Preparation 1), there are obtained the corresponding formula-XL compounds, 3β-benzoyloxy-5β-hydroxy-2α-(3α-hydroxy-4-methyl-trans-1-octenyl)-1β-cyclopentaneacetic acid γ-lactone and 3β-benzoyloxy-5β-hydroxy-2α-(3β-hydroxy-4-methyl-trans-1-octenyl)-1β-cyclopentaneacetic acid γ-lactone.

Thereafter, following the procedures of Examples 18-22, inclusive, the above 3α-hydroxy-4-methyloctenyl intermediates are transformed to the above title compounds.

Likewise following the procedures of Examples 18–22, inclusive, but employing the 3β-hydroxy-4-methyloctenyl intermediates above, there are obtained the corresponding C-15 epimers, namely 16-methyl-8β,11β,12α,15β-PGE$_2$, methyl ester.

EXAMPLE 40

16-Methyl-8β,9α,11β,12α-PGF$_2$, Methyl Ester (Formula LIV: M is

Q is —CH(CH$_3$)—(CH$_2$)$_3$—CH$_3$, and R$_{12}$ is methyl) and 16-Methyl-8β,9β,11β,12α-PGF$_2$, Methyl Ester (Formula LIV: M is

Q is —CH(CH$_3$)—(CH$_2$)$_3$—CH$_3$, and R$_{12}$ is methyl).

Refer to Chart D. Following the procedures of Example 12, the 15α formula-LIII 16-methyl-8β,11β,12α-PGE$_2$, methyl ester of Example 39 is reduced with sodium borohydride to the title compounds, which are separated by silica gel chromatography.

Likewise following the procedures of Example 12, but employing the 15β formula-LIII 16-methyl-8β,11β,12α,15β-PGE$_2$, methyl ester following Example 39, there are obtained the corresponding C-15 epimers, namely 16-methyl-8β,9α,11β,12α,15β-PGF$_2$, methyl ester, and 16-methyl-8β,9β,11β,12α,15β-PGF$_2$, methyl ester.

EXAMPLE 41

16,16-Dimethyl-8β,12α-PGE$_2$, Methyl Ester (Formula XXXIV: M is

Q is —CH(CH$_3$)$_2$—(CH$_2$)$_3$—CH$_3$, and R$_{12}$ is methyl).

Refer to Charts A and B. Following the procedures of Examples 5 and 6, but replacing the ylide of Example 5 with the ylide prepared from dimethyl 2-oxo-3,3-dimethylheptylphosphonate (Preparation 2), there are obtained the corresponding formula-XXV compounds, 3α-benzoyloxy-5β-hydroxy-2α-(3α-hydroxy-4,4-dimethyl-trans-1-octenyl)-1β-cyclopentaneacetic acid γ-lactone and 3α-benzoyloxy-5β-hydroxy-2α-(3β-hydroxy-4,4-dimethyl-trans-1-octenyl)-1β-cyclopentaneacetic acid γ-lactone.

Thereafter, following the procedures of Examples 7–11, inclusive, the above 3α-hydroxy-4,4-dimethyloctenyl) intermediate is transformed to the above title compound (42% yield having R$_f$ 0.5 in ethyl acetate; mass spectral peaks (for the trimethylsilyl derivative) at 583, 523, 507, 439, 349, and 295; and NMR peaks at 5.88–5.19, 4.50–4.29, 3.98–3.85, 3.67 (singlet), 3.10–2.85, 2.70–0.70, 1.25 (singlet) and 0.88 (singlet) δ.

Likewise following the procedures of Examples 7–11, inclusive, but employing the 3β-hydroxy-4,4-dimethyloctenyl intermediate above, there is obtained the corresponding C-15 epimer, namely 16,16-dimethyl-8β,12α,15β-PGE$_2$, methyl ester (56% yield) having R$_f$ 0.4 in ethyl acetate; mass spectral peaks (for the trimethylsilyl derivative) at 537, 523, 507, 439, 349, and 295; and NMR peaks at 5.87–5.70, 5.53–5.24, 4.48–4.28, 3.98–3.77, 3.67 (singlet), 3.30–0.71, 1.25 (singlet) and 0.90 (singlet) δ.

EXAMPLE 42

16,16-Dimethyl-8β,9α,12α-PGF$_2$, Methyl Ester (Formula XXXV: M is

Q is —C(CH$_3$)$_2$—(CH$_2$)$_3$—CH$_3$, and R$_{12}$ is methyl) and 16,16-Dimethyl-8β,9β,12α-PGF$_2$, Methyl Ester (Formula XXXV: M is

Q is —C(CH$_3$)$_2$—(CH$_2$)$_3$—CH$_3$, and R$_{12}$ is methyl).

Refer to Chart B. Following the procedures of Example 12, but replacing the 15α formula-XXXIV PGE$_2$ analog of that example with the product of Example 41, namely 16,16-dimethyl-8β,12α-PGE$_2$, methyl ester, the above title compounds are obtained. The 9α compound (obtained in 62% yield) has R$_f$ 0.3 (TLC on silica gel in ethyl acetate); mass spectral peaks (for the trimethylsilyl derivative) at 611, 597, 581, 555, 522, 513, 507, 491, 423, 397, 333, 307, and 217; and NMR peaks at 5.86–5.30, 4.24–3.75, 3.67 (singlet), 3.17 (singlet), 2.50–0.37, 1.25 (singlet), and 0.90 (singlet). Following the procedures of Example 13, the 9β compound is obtained in 69% yield, having R$_f$ 0.3 (TLC on silica gel in ethyl acetate); mass spectral peaks (for trimethylsilyl derivative) at 597, 581, 522, 513, 423, 397, 333, 307, and 217; and NMR peaks at 5.50–5.26, 4.47–3.77, 3.67 (singlet), 2.71–0.63, 1.25 (singlet) and 0.88 (singlet) δ.

Likewise following the procedures of Example 12, but employing the 15β analog, namely 16,16-dimethyl-8β,12α,15β-PGE$_2$, methyl ester, obtained following Example 41, there are obtained the corresponding C-15 epimers, namely 16,16-dimethyl-8β,9α,12β,15β-PGF$_2$, methyl ester, and 16,16-dimethyl-8β,8β,12α,15β-PGF$_2$, methyl ester. The 9α compound (obtained in 73% yield) has R$_f$ 0.2 (TLC on silica gel in ethyl acetate); mass spectral peaks (for the trimethylsilyl derivative) at 611, 597, 581, 555, 522, 513, 507, 491, 423, 397, 333, 307, and 217; and NMR peaks at 611, 597, 581, 555, 522, 513, 507, 491, 423, 397, 333, 307, and 217 δ. Following the procedure of Example 13, the 9β compound is obtained in 91% yield, having m.p. 41°–42.8° C. (from diethyl ether-hexane); R$_f$ 0.2 (TLC on silica gel in ethyl acetate); mass spectral peaks (for trimethylsilyl derivative) 597, 581, 555, 522, 513, 423, 397, 333, 307, and 217; and NMR peaks at 5.50–5.27, 4.52–3.57, 3.67 (singlet), 3.01–0.63, 1.25 (singlet), and 0.90 (singlet) δ.

EXAMPLE 43

16,16-Dimethyl-8β,11β,12α-PGE$_2$, Methyl Ester (Formula XLVI: M''' is

Q is —C(CH$_3$)$_2$—(CH$_2$)$_3$—CH$_3$, R$_8$ is hydrogen, and R$_{12}$ is methyl).

Refer to Charts A and C. Following the procedures of Examples 16 and 17, but replacing the ylide of Example 16 with the ylide prepared from dimethyl 2-oxo-3,3-dimethylheptylphosphonate (Preparation 2), there are obtained the corresponding formula-XL compounds, 3β-benzoyloxy-5β-hydroxy-2α-(3α-hydroxy-4,4-dimethyl-trans-1-octenyl)-1β-cyclopentaneacetic acid γ-lactone and 3β-benzoyloxy-5β-hydroxy-2α-(3β-hydroxy-4,4-dimethyl-trans-1-octenyl)-1β-cyclopentaneacetic acid γ-lactone.

Thereafter, following the procedures of Examples 18–22, inclusive, the above 3α-hydroxy-4,4-dimethyloctenyl intermediate is transformed to the above title compound.

Likewise following the procedures of Examples 18–22, inclusive, but employing the 3β-hydroxy-4,4-dimethyloctenyl intermediate above, there is obtained the corresponding C-15 epimer, namely 16,16-dimethyl-8β,11β,12α,15β-PGE$_2$, methyl ester.

EXAMPLE 44

16,16-Dimethyl-8β,9α,11β,12α-PGF$_2$, Methyl Ester (Formula XXXV: M is

Q is —C(CH$_3$)$_2$—(CH$_2$)$_3$—CH$_3$, and R$_{12}$ is methyl) and 16,16-Dimethyl-8β,9β,11β,12α-PGF$_2$, Methyl Ester (Formula XXXV: M is

Q is —C(CH$_3$)$_2$—(CH$_2$)$_3$—CH$_3$, and R$_{12}$ is methyl).

Refer to Chart B. Following the procedures of Example 12, but replacing the 15α formula-XXXIV PGE$_2$ analog of that example with the product of Example 43, namely 16,16-dimethyl-8β,11β,12α-PGE$_2$, methyl ester, the above title compounds are obtained.

Likewise following the procedures of Example 12, but employing the 15β analog, namely 16,16-dimethyl-8β,11β,12α,-15β-PGE$_2$, methyl ester, obtained following Example 43, there are obtained the corresponding C-15 epimers, namely 16,16-dimethyl-8β,9α,11β,-12α,15β-PGF$_2$, methyl ester, and 16,16-dimethyl-8β,9β,11β,12α,15β-PGF$_2$, methyl ester.

EXAMPLE 45

17-Phenyl-18,19,20-trinor-8β,12α-PGE$_2$, Methyl Ester (Formula XXXIV: M is

Q is

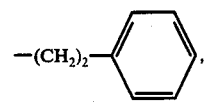

and R$_{12}$ is methyl).

Refer to Charts A and B. Following the procedures of Examples 5 and 6, but replacing the ylide of Example 5 with the ylide prepared from dimethyl 2-oxo-4-phenylbutylphosphonate (Preparation 3), there are obtained the corresponding formula-XXV compounds, 3α-benzoyloxy-5β-hydroxy-2α-(3α-hydroxy-5-phenyl-trans-1-pentenyl)-1β-cyclopentaneacetic acid γ-lactone and 3α-benzoyloxy-5β-hydroxy-2α-(3β-hydroxy-5-phenyl-trans-1-pentenyl)-1β-cyclopentaneactic acid γ-lactone.

Thereafter, following the procedures of Examples 7–11, inclusive, the above 3α-hydroxy-5-phenylpentenyl intermediate is transformed to the above title compound (76% yield) having R$_f$0.5 (TLC on silica gel in ethyl acetate) and NMR peaks at 7.20 (singlet), 5.87–5.67, 5.48–5.20, 4.47–3.90, 3.63 (singlet), and 3.58–1.05 δ.

Likewise following the procedures of Examples 7–11, inclusive, but employing the 3β-hydroxy-5-phenylpentenyl intermediate above, there is obtained the corresponding C-15 epimer, namely 17-phenyl-18,19,20-trinor-8β,12α,15β-PGE$_2$, methyl ester.

EXAMPLE 46

17-Phenyl-18,19,20-trinor-8β,9α,12α-PGF$_2$, Methyl Ester (Formula XXXV: M is

Q is

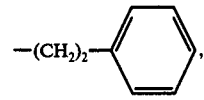

R$_{12}$ is methyl) and 17-Phenyl-18,19,20-trinor-8β,9β,12α-PGF$_2$, Methyl Ester (Formula XXXV: M is

Q is

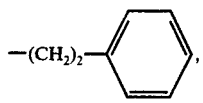

$R_{12}$ is methyl).

Refer to Chart B. Following the procedures of Example 12, but replacing the 15α formula-XXXIV PGE$_2$ analog of that example with the product of Example 45, namely 17-phenyl-18,19,20-trinor-8β,12α-PGE$_2$, methyl ester, the above title compounds are obtained. The 9α compound (obtained in 62% yield) has $R_f$ 0.5 (TLC on silica gel in ethyl acetate) and NMR peaks at 7.2 (singlet), 5.87–5.67, 5.48–5.20, 4.47–3.90, 3.63 (singlet), and 3.58–1.05 δ. The 9β compound (obtained in 14% yield by the procedures of Example 12 and 93% yield by the procedures of Example 13) has $R_f$ 0.3 (TLC on silica gel in 30% acetone in dichloromethane) and NMR peaks at 7.23 (singlet), 5.80–5.23, 4.48–3.82, 3.65 (singlet), and 3.02–0.80 δ.

Likewise following the procedures of Example 12, but employing the 15β analog, namely 17-phenyl-18,19,20-trinor-8β,12α,15β-PGE$_2$, methyl ester, obtained following Example 45, there are obtained the corresponding C-9 epimers, namely 17-phenyl-18,19,20-trinor-8β,9α,12α,15β-PGF$_2$, methyl ester, and 17-phenyl-18,19,20-trinor-8β,9β,12α,15β-PGF$_2$, methyl ester.

EXAMPLE 47

17-Phenyl-18,19,20-trinor-8β,11β,12α-PGE$_2$, Methyl Ester (Formula XLVI:M''' is

Q is

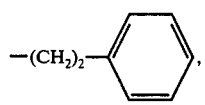

$R_8$ is hydrogen, and $R_{12}$ is methyl).

Refer to Charts A and C. Following the procedures of Examples 16 and 17, but replacing the ylide of Example 16 with the ylide prepared from dimethyl 2-oxo-4-phenylbutylphosphonate (Preparation 3), there are obtained the corresponding formula-XL compounds, 3β-benzoyloxy-5β-hydroxy-2α-(3α-hydroxy-5-phenyl-trans-1-pentenyl)-1β-cyclopentaneacetic acid γ-lactone and 3β-benzoyloxy-5β-hydroxy-2α-(3β-hydroxy-5-phenyl-trans-1-pentenyl)-1β-cyclopentaneacetic acid γ-lactone.

Thereafter, following the procedures of Examples 18–22, inclusive, the above 3α-hydroxy-5-phenylpentenyl intermediate is transformed to the above title compound.

Likewise following the procedures of Examples 18–22, inclusive, but employing the 3β-hydroxy-5-phenylpentenyl intermediate above, there is obtained the corresponding C-15 epimer, namely 17-phenyl-18,19,20-trinor-8β,11β,12α,15β-PGE$_2$, methyl ester.

EXAMPLE 48

17-Phenyl-18,19,20-trinor-8β,9α,11β,12α-PGF$_2$, Methyl Ester (Formula XXXV: M is

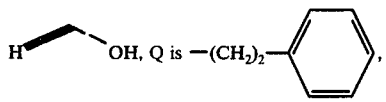

and $R_{12}$ is methyl) and 17-Phenyl-18,19,20-trinor-8β,9β,12α-PGF$_2$, Methyl Ester (Formula XXXV: M is

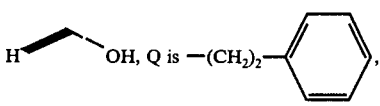

and $R_{12}$ is methyl).

Refer to Chart B. Following the procedures of Example 12, but replacing the 15α formula-XXXIV PGE$_2$ analog of that example with the product of Example 47, namely 17-phenyl-18,19,20-trinor-8β,11β,12α-PGE$_2$, methyl ester, the above title compounds are obtained.

Likewise following the procedures of Example 12, but employing the 15β analog, namely 17-phenyl-18,19,20-trinor-8β,11β,12α,15β-PGE$_2$, methyl ester, obtained following Example 47, there are obtained the corresponding C-9 epimers, namely 17-phenyl-18,19,20-trinor-8β,9α,11β,12α,15β-PGF$_2$, methyl ester, and 17-phenyl-18,19,20-trinor-8β,9β,11β,12α,15β-PGF$_2$, methyl ester.

EXAMPLE 49

3α-Benzoyloxy-5β-hydroxy-2α-(3α-methoxy-trans-1-octenyl)-1β-cyclopentaneacetic Acid γ-Lactone (Formula LVI: $M^{IV}$ is

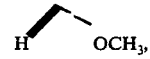

Q is n-pentyl, and $R_3$ is benzoyl)

Refer to Chart E. A mixture of the formula-XXVI alpha hydroxy compound (Example 6, 2.0 g.), silver oxide (4.0 g.), and 50 ml. of methyl iodide is stirred and heated at reflux for 68 hr. The mixture is cooled and filtered, and the filtrate concentrated. The residue is subjected to silica gel chromatography to obtain the formula-LVI title compound.

Following the procedure of Example 49, but replacing the methyl iodide of that example with other alkyl halides, there are obtained the corresponding formula-LVI alkyl esters. Thus, with methyl bromide, ethyl chloride, isopropyl iodide, butyl bromide, or pentyl iodide, there are obtained the formula-LVI compound in which $R_{22}$ is methyl, ethyl, isopropyl, n-butyl or n-pentyl.

EXAMPLE 50

8β,9β,12α-PGF₂, Methyl Ester, 15-Methyl Ether (Formula LXI: M¹ᵛ is

Q is n-pentyl, and R₁₂ is methyl); and 8β,12α-PGE₂, Methyl Ester, 15-Methyl Ether (Formula LXIV: M¹ᵛ is

Q is n-pentyl, and R₁₂ is methyl).

Refer to Chart E. Following the procedures of Example 7, 8, 9, 10, and 11, but starting with the formula-LVI 3α-methoxyoctenyl compound of Example 49, there are obtained the corresponding intermediates and products as follows:

3α,5β-dihydroxy-2α-(3α-methoxy-trans-1-octenyl)-1β-cyclopentaneacetic acid γ-lactone (formula LVII) and its tetrahydropyranyl ether (formula LVIII);

3α,5β-dihydroxy-2α-(3α-methoxy-trans-1-octenyl)-1β-cyclopentaneacetaldehyde γ-lactol, tetrahydropyranyl ether (formula LIX);

8β,9β,12α-PGF₂, methyl ester, 11-tetrahydropyranyl ether, 15-methyl ether (formula LX); 8β,12α-PGE₂, methyl ester, 11-tetrahydropyranyl ether, 15-methyl ether (formula LXIII);

and the title compounds.

EXAMPLE 51

15-Methyl-8β,11β,12α-PGE₂ (Formula LIII: M is

Q is n-pentyl, and R₁₂ is hydrogen).

There is first prepared an esterase composition from Plexaura homomalla, for which see W. P. Schneider et al., J. Am. Chem. Soc. 94, 2122 (1972). Freshly harvested colony pieces of Plexaura homomalla (Esper), 1792, forma S (10 kg.), are chopped into pieces less than 3 mm. in their longest dimension, and then covered with about three volumes (20 l.) of acetone. The mixture is stirred at about 25° C. for about one hour. The solids are separated by filtration, washed with 1-2 liters of acetone, air dried, and finally stored at about −20° C. as a coarse enzymatic powder.

A suspension of the above powder (2.5 g.) in 25 ml. of water is combined with a solution of 15-methyl-8β,11β,12α-PGE₂, methyl ester (Example 30, 0.5 g.) in about 0.8 ml. of ethanol previously acidified to pH 6 with phosphoric acid. The mixture is stirred at about 25° C. for 24 hrs. Then, 50 ml. of acetone is added, the mixture is stirred briefly and filtered, and the filtrate is concentrated under reduced pressure. The aqueous residue is acidified to pH 3.5 with citric acid and extracted with dichloromethane. The combined extracts are concentrated under reduced pressure to the title compound.

Following the procedure of Example 51, but replacing the methyl ester of that example with the methyl esters of and following Examples 11, 12, and 13 there are obtained the corresponding free acids, namely 8β,12α-PGE₂
8β,12α,15β-PGE₂
8β,12α-PGA₂
8β,12α,15β-PGA₂
8β,9α,12α-PGF₂
8β,9α,12α,15β-PGF₂
8β,9β,12α-PGF₂ and
8β,9β,12α,15β-PGF₂

Likewise, applying the procedure of Example 51 to the methyl esters of and following Examples 22, 23, 24, 29, 30, 31, and 34–50, inclusive, there are obtained the corresponding free acids.

EXAMPLE 52

8β,12α-PGE₂, Ethyl Ester

A solution of diazoethane (about 0.5 g.) in 25 ml. of diethyl ether (25 ml.) is added to a solution of 8β,12α-PGE₂ (following Example 51, 50 mg.) in 25 ml. of a mixture of methanol and diethyl ether (1:1). The mixture is allowed to stand at 25° C. for 5 min. Then, the mixture is concentrated to give the title compound.

Following the procedure of Example 52, each of the other 8β,12α-PGE₂ or -PGF₂ type free acids defined above is converted to the corresponding ethyl ester.

Also following the procedure of Example 52, but using in place of the diazoethane, diazobutane, 1-diazo-2-ethylhexane, and diazocyclohexane, there are obtained the corresponding butyl, 2-ethylhexyl, and cyclohexyl esters of 8β,12α,15α-PGE₂. In the same manner, each of the other 8β,12α-PGE₂ or -PGF₂ type free acids defined above is converted to the corresponding butyl, 2-ethylhexyl, and cyclohexyl esters.

EXAMPLE 53

8β,12α-PGE₂, Methyl Ester, Diacetate

Acetic anhydride (5 ml.) and pyridine (5 ml.) are mixed with 8β,12α-PGE₂, methyl ester (following Example 51, 20 mg.), and the mixture is allowed to stand at 25° C. for 18 hrs. The mixture is then cooled to 0° C., diluted with 50 ml. of water, and acidified with 5% hydrochloric acid to pH 1. That mixture is extracted with ethyl acetate. The extract is washed successively with 5% hydrochloric acid, 5% aqueous sodium bicarbonate solution, water, and brine, dried and concentrated to give the title compound.

Following the procedure of Example 53, but replacing the acetic anhydride with propionic anhydride, isobutyric anhydride, and hexanoic acid anhydride, there are obtained the corresponding dipropionate, diisobutyrate and dihexanoate derivatives of 8β,12α-PGE₂, methyl ester.

Also following the procedure of Example 53, but replacing the 8β,12α-PGE₂ compound with 8β,9α,12α-PGF₂ and 8β,9β,12α-PGF₂ there are obtained the corresponding triacetate derivatives of the 8β,12α-PGF₂ compounds.

Also following the procedure of Example 53, each of the 8β,12α-PGE₂ or -PGF₂ type esters and free acids defined above is transformed to the corresponding acetates, propionates, isobutyrates, and hexanoates, the PGE-type derivatives being dicarboxyacylates, and the PGF-type derivatives being tricarboxyacylates.

EXAMPLE 54

8β,12α-PGE$_2$ Sodium Salt

A solution of 8β,12α-PGE$_2$ (following Example 51, 100 mg.) in 50 ml. of a water-ethanol mixture (1:1) is cooled to 5° C. and neutralized with an equivalent amount of 0.1 N aqueous sodium hydroxide solution. The neutral solution is evaporated to give the title compound.

Following the procedure of Example 54 but using potassium hydroxide, calcium hydroxide, tetramethylammonium hydroxide, and benzyltrimethylammonium hydroxide in place of sodium hydroxide, there are obtained the corresponding salts of 8β,12α-PGE$_2$.

Also following the procedure of Example 54 each of the 8β,12α-PGE-type or -PGF-type acids defined above is transformed to the sodium, potassium, calcium, tetramethylammonium, and benzyltrimethylammonium salts.

I claim:

1. An optically active compound of the formula

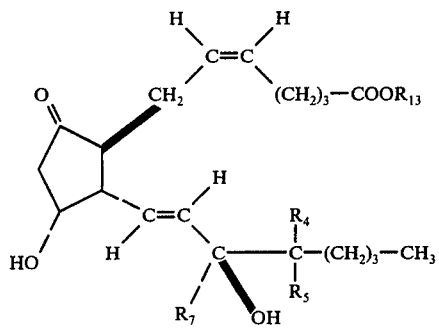

wherein $R_4$, $R_5$, and $R_7$ are hydrogen or methyl, being the same or different;
wherein $R_{13}$ is hydrogen, alkyl of one to 10 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; including the lower alkanoates thereof, and the pharmacologically acceptable salts thereof wherein $R_{13}$ is hydrogen.

2. A compound according to claim 1, wherein $R_7$ is methyl.

3. 15-Methyl-8β,12α,15β-PGE$_2$, a compound according to claim 2.

4. 15-Methyl-8β,12α,15β-PGE$_2$, methyl ester, a compound according to claim 2.

5. A compound according to claim 1, wherein $R_4$ and $R_5$ are methyl.

6. 16,16-Dimethyl-8β,12α,15β-PGE$_2$, a compound according to claim 5.

7. 16,16-Dimethyl-8β,12α,15β-PGE$_2$, methyl ester a compound according to claim 5.

8. 8β,12α,15β-PGE$_2$, a compound according to claim 1.

9. An optically active compound of the formula

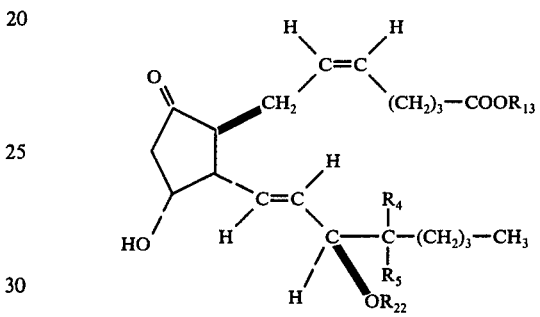

wherein $R_4$, $R_5$, and $R_7$ are hydrogen or methyl, being the same or differnt;
wherein $R_{13}$ is hydrogen, alkyl of one to 10 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive;
wherein $R_{22}$ is alkyl of one to 4 carbon atoms, inclusive; including the lower alkanoates thereof, and the pharmacologically acceptable salts thereof wherein $R_{13}$ is hydrogen.

* * * * *

UNITED STATES PATENT AND TRADEMARK OFFICE
CERTIFICATE OF CORRECTION

PATENT NO. : 4,096,342
DATED : June 20, 1978
INVENTOR(S) : Ernest W. Yankee

It is certified that error appears in the above-indentified patent and that said Letters Patent is hereby corrected as shown below:

On the title page, item [63]

The "Related U.S. Application Data" should read

-- Continuation of Ser. No. 518,645, Oct. 29, 1974, abandoned; division of Ser. No. 374,405, June 28, 1973, U.S. Patent 4,100,355; continuation-in-part of Ser. No. 289,317, Sep. 15, 1972, abandoned. --

Column 1, lines 6-9

The Cross Reference to Related Applications should read

-- This is a continuation of application Ser. No. 518,645, filed Oct. 29, 1974, now abandoned; which is a division of Ser. No. 374,405, filed June 28, 1973, now U.S. Patent 4,100,355; which is a continuation-in-part of Ser. No. 289,317, filed Sep. 15, 1972, now abandoned. --.

Signed and Sealed this

Tenth Day of August, 1993

Attest:

MICHAEL K. KIRK

Attesting Officer

Acting Commissioner of Patents and Trademarks